(12) United States Patent
Gowans et al.

(10) Patent No.: US 11,759,144 B2
(45) Date of Patent: Sep. 19, 2023

(54) SYSTEMS AND METHODS FOR INSPECTION OF ENCAPSULATION AND COMPONENTS IN SENSOR EQUIPPED WOUND DRESSINGS

(71) Applicant: Smith & Nephew PLC, Watford (GB)

(72) Inventors: Philip Gowans, Doncaster (GB); Edward Yerbury Hartwell, Hull (GB); Allan Kenneth Frazer Grugeon Hunt, Beverley (GB); Lee Ian Partington, Hessle (GB); Marcus Damian Phillips, Wakefield (GB); Daniel Lee Steward, Kingston upon Hull (GB); Charlotte Urwin, Hull (GB)

(73) Assignee: Smith & Nephew PLC, Watford (GB)

( * ) Notice: Subject to any disclaimer, the term of this patent is extended or adjusted under 35 U.S.C. 154(b) by 524 days.

(21) Appl. No.: 16/645,761

(22) PCT Filed: Sep. 7, 2018

(86) PCT No.: PCT/EP2018/074176
§ 371 (c)(1),
(2) Date: Mar. 9, 2020

(87) PCT Pub. No.: WO2019/048624
PCT Pub. Date: Mar. 14, 2019

(65) Prior Publication Data
US 2020/0281519 A1    Sep. 10, 2020

Related U.S. Application Data

(60) Provisional application No. 62/556,479, filed on Sep. 10, 2017.

(51) Int. Cl.
*A61B 5/00* (2006.01)
*A61B 5/1455* (2006.01)
(Continued)

(52) U.S. Cl.
CPC ............ *A61B 5/445* (2013.01); *A61B 5/0261* (2013.01); *A61B 5/0531* (2013.01);
(Continued)

(58) Field of Classification Search
CPC ..... A61B 5/445; A61B 5/0261; A61B 5/0531; A61B 5/1455; A61B 5/6802;
(Continued)

(56) References Cited

U.S. PATENT DOCUMENTS

| 3,896,802 A | 7/1975 | Williams |
| 4,334,530 A | 6/1982 | Hassell |

(Continued)

FOREIGN PATENT DOCUMENTS

| CN | 105232229 A | 1/2016 |
| CN | 105395184 A | 3/2016 |

(Continued)

OTHER PUBLICATIONS

"Varun Ratta, Crystallization, Morphology, Thermal Stability and Adhesive Properties of Novel High Performance Semicrystalline Polyimides—Chapter 4 Polyimides as Adhesives:—Literature review, Virginia Tech, pp. 102-124, https://vtechworks.lib.vt.edu/handle/10919/27771" (Year: 1999).*

(Continued)

*Primary Examiner* — Joseph M Dietrich
*Assistant Examiner* — Michael T. Holtzclaw
(74) *Attorney, Agent, or Firm* — Knobbe, Martens Olson & Bear, LLP

(57) ABSTRACT

Disclosed herein are embodiments of methods of inspection and manufacture of flexible printed circuit boards and flexible sensor sheets, and apparatuses such as wound dressing components utilizing the same. The methods can comprise applying a coating material to a flexible printed circuit board, wherein the coating material comprises a material (Continued)

that will fluoresce when exposed to UV or visible light and the flexible printed circuit board comprises one or more electronic components. The coated flexible printed circuit board can be positioned under UV or visible light to cause the coating material to fluoresce.

4 Claims, 21 Drawing Sheets

(51) Int. Cl.
    *C09D 175/04*     (2006.01)
    *C09J 9/00*     (2006.01)
    *G01N 21/64*     (2006.01)
    *A61B 5/026*     (2006.01)
    *A61B 5/0531*     (2021.01)
    *A61F 13/02*     (2006.01)
    *A61F 13/08*     (2006.01)
    *A61M 1/00*     (2006.01)

(52) U.S. Cl.
    CPC .......... *A61B 5/1455* (2013.01); *A61B 5/6802* (2013.01); *A61F 13/0206* (2013.01); *A61F 13/08* (2013.01); *A61M 1/90* (2021.05); *C09D 175/04* (2013.01); *C09J 9/00* (2013.01); *G01N 21/64* (2013.01); *A61B 2562/0215* (2017.08); *A61B 2562/12* (2013.01)

(58) Field of Classification Search
    CPC ........ A61B 2562/0215; A61B 2562/12; A61B 2090/3966; A61B 2560/0468; A61B 5/01; A61B 5/742; A61B 5/6833; A61B 5/6801; A61F 13/0206; A61F 13/08; A61M 1/90; C09D 175/04; C09J 9/00; G01N 21/64
    See application file for complete search history.

(56) References Cited

U.S. PATENT DOCUMENTS

| | | | |
|---|---|---|---|
| 5,090,410 A | 2/1992 | Saper et al. | |
| 5,253,654 A | 10/1993 | Thomas et al. | |
| 5,635,201 A | 6/1997 | Fabo | |
| 5,642,096 A | 6/1997 | Leyerer et al. | |
| 5,678,448 A | 10/1997 | Fullen et al. | |
| 5,690,610 A | 11/1997 | Ito et al. | |
| 5,836,990 A | 11/1998 | Li | |
| 6,095,992 A | 8/2000 | Augustine | |
| 6,178,342 B1 | 1/2001 | Borgos et al. | |
| 6,381,482 B1 | 4/2002 | Jayaraman et al. | |
| 6,517,484 B1 | 2/2003 | Wilk et al. | |
| 6,551,252 B2 | 4/2003 | Sackner et al. | |
| 6,731,987 B1 | 5/2004 | McAdams et al. | |
| 7,077,832 B2 | 7/2006 | Fleischmann | |
| 7,088,591 B2 | 8/2006 | Kishimoto et al. | |
| 7,201,063 B2 | 4/2007 | Taylor | |
| 7,206,623 B2 | 4/2007 | Blank et al. | |
| 7,289,205 B2 | 10/2007 | Yaroslavsky et al. | |
| 7,316,652 B2 | 1/2008 | Dalgaard et al. | |
| 7,429,255 B2 | 9/2008 | Thompson | |
| 7,520,875 B2 | 4/2009 | Bernabei | |
| 7,521,292 B2 | 4/2009 | Rogers et al. | |
| 7,569,742 B2 | 8/2009 | Haggstrom et al. | |
| 7,625,117 B2 | 12/2009 | Haslett et al. | |
| 7,687,678 B2 | 3/2010 | Jacobs | |
| 7,846,141 B2 | 12/2010 | Weston | |
| 7,877,866 B1 | 2/2011 | Greenberg et al. | |
| 7,884,258 B2 | 2/2011 | Boehringer et al. | |
| 7,904,133 B2 | 3/2011 | Gehman et al. | |
| 7,922,676 B2 | 4/2011 | Daskal et al. | |
| 7,942,869 B2 | 5/2011 | Houbolt et al. | |
| 7,945,302 B2 | 5/2011 | McAdams | |
| 8,019,401 B1 | 9/2011 | Smith et al. | |
| 8,032,210 B2 | 10/2011 | Finneran et al. | |
| 8,060,174 B2 | 11/2011 | Simpson et al. | |
| 8,079,247 B2 | 12/2011 | Russell et al. | |
| 8,111,165 B2 | 2/2012 | Ortega et al. | |
| 8,116,841 B2 | 2/2012 | Bly et al. | |
| 8,182,425 B2 | 5/2012 | Stamatas et al. | |
| 8,238,996 B2 | 8/2012 | Burnes et al. | |
| 8,241,231 B2 | 8/2012 | Bausewein et al. | |
| 8,332,053 B1 | 12/2012 | Patterson et al. | |
| 8,333,874 B2 | 12/2012 | Currie | |
| 8,366,692 B2 | 2/2013 | Weston et al. | |
| 8,480,641 B2 | 7/2013 | Jacobs | |
| 8,579,872 B2 | 11/2013 | Coulthard et al. | |
| 8,644,911 B1 | 2/2014 | Panasyuk et al. | |
| 8,663,106 B2 | 3/2014 | Stivoric et al. | |
| 8,682,442 B2 | 3/2014 | McAdams | |
| 8,783,948 B2 | 7/2014 | Panda et al. | |
| 8,788,009 B2 | 7/2014 | Greene et al. | |
| 8,800,386 B2 | 8/2014 | Taylor | |
| 8,818,478 B2 | 8/2014 | Scheffler et al. | |
| 8,848,187 B2 | 9/2014 | Uematsu et al. | |
| 8,894,590 B2 | 11/2014 | Lamoise et al. | |
| 8,925,392 B2 | 1/2015 | Esposito et al. | |
| 8,934,957 B2 | 1/2015 | Dias et al. | |
| 8,934,965 B2 | 1/2015 | Rogers et al. | |
| 8,943,897 B2 | 2/2015 | Beauvais et al. | |
| 8,948,839 B1 | 2/2015 | Longinotti-Buitoni et al. | |
| 8,997,588 B2 | 4/2015 | Taylor | |
| 9,000,251 B2 | 4/2015 | Murphy et al. | |
| 9,042,075 B2 | 5/2015 | Borini et al. | |
| 9,192,531 B2 | 11/2015 | Wu | |
| 9,220,455 B2 | 12/2015 | Sarrafzadeh et al. | |
| 9,226,402 B2 | 12/2015 | Hsu | |
| 9,282,897 B2 | 3/2016 | Ross, Jr. et al. | |
| 9,314,175 B2 | 4/2016 | Jacofsky et al. | |
| 9,320,473 B2 | 4/2016 | Shuler | |
| 9,372,123 B2 | 6/2016 | Li et al. | |
| 9,378,450 B1 | 6/2016 | Mei et al. | |
| 9,386,947 B2 | 7/2016 | Johnson | |
| 9,393,354 B2 | 7/2016 | Freedman et al. | |
| 9,402,988 B2 | 8/2016 | Buchanan et al. | |
| 9,408,573 B2 | 8/2016 | Welch et al. | |
| 9,427,179 B2 | 8/2016 | Mestrovic et al. | |
| 9,439,599 B2 | 9/2016 | Thompson et al. | |
| 9,483,726 B2 | 11/2016 | Mei et al. | |
| 9,494,474 B2 | 11/2016 | Servati et al. | |
| 9,511,215 B2 | 12/2016 | Skiba | |
| 9,516,758 B2 | 12/2016 | Arora et al. | |
| 9,526,439 B2 | 12/2016 | Connelly et al. | |
| 9,554,484 B2 | 1/2017 | Rogers et al. | |
| 9,572,507 B2 | 2/2017 | Moore et al. | |
| 9,582,072 B2 | 2/2017 | Connor | |
| 9,585,620 B2 | 3/2017 | Paquet et al. | |
| 9,587,991 B2 | 3/2017 | Padiy | |
| 9,592,007 B2 | 3/2017 | Nuovo et al. | |
| 9,603,560 B2 | 3/2017 | Monty et al. | |
| 9,610,388 B2 | 4/2017 | Aceto et al. | |
| 9,613,911 B2 | 4/2017 | Rogers et al. | |
| 9,629,584 B2 | 4/2017 | Macia et al. | |
| 9,675,238 B2 | 6/2017 | Iida et al. | |
| 9,687,195 B2 | 6/2017 | Sims et al. | |
| 9,717,565 B2 | 8/2017 | Blair | |
| 9,829,471 B2 | 11/2017 | Hammond et al. | |
| 9,907,103 B2 | 2/2018 | Chen et al. | |
| 10,004,643 B2 | 6/2018 | Luckemeyer et al. | |
| 10,046,096 B2 | 8/2018 | Askem et al. | |
| 10,080,524 B1 | 9/2018 | Xi | |
| 10,086,117 B2 | 10/2018 | Locke et al. | |
| 10,117,705 B2 | 11/2018 | Chernov et al. | |
| 10,152,789 B2 | 12/2018 | Carnes et al. | |
| 10,182,740 B2 | 1/2019 | Tonar et al. | |
| 10,207,031 B2 | 2/2019 | Toth | |
| 10,209,213 B2 | 2/2019 | Kang et al. | |
| 10,226,212 B2 * | 3/2019 | Duesterhoft ............. | A61B 5/01 |
| 10,285,620 B2 | 5/2019 | Jung et al. | |
| 10,321,862 B2 | 6/2019 | Dalene et al. | |
| 10,463,773 B2 | 11/2019 | Haggstrom et al. | |
| 10,857,038 B2 | 12/2020 | Zamierowski et al. | |

(56) References Cited

U.S. PATENT DOCUMENTS

| | | |
|---|---|---|
| 11,026,847 B2 | 6/2021 | Piotrowski et al. |
| 11,229,553 B2 | 1/2022 | Chen et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0230747 A1* | 9/2011 | Rogers .................. A61L 31/047 600/377 |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274629 A1 | 10/2013 | Duesterhoft et al. |
| 2013/0317367 A1 | 11/2013 | Shuler |
| 2014/0012094 A1* | 1/2014 | Das ...................... A61K 9/703 600/300 |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad et al. |
| 2016/0022223 A1 | 1/2016 | Grundfest et al. |
| 2016/0029900 A1 | 2/2016 | Laplante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |

(56) References Cited

U.S. PATENT DOCUMENTS

| | | |
|---|---|---|
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0079846 A1 | 3/2017 | Locke et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0127525 A1* | 5/2017 | Schönholz ........... H05K 3/4611 |
| 2017/0146474 A1 | 5/2017 | Bedell et al. |
| 2017/0153184 A1* | 6/2017 | Bogaki .................. G07D 7/12 |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1* | 7/2017 | Cernasov ......... A61F 13/00021 |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0365571 A1* | 12/2019 | O'Mahony .......... A61B 5/6833 |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0147407 A1 | 5/2020 | Efremkin |
| 2020/0188180 A1* | 6/2020 | Akbari ................ A61F 13/0246 |
| 2020/0330258 A1 | 10/2020 | Hansen et al. |
| 2021/0212855 A1 | 7/2021 | Hansen et al. |
| 2021/0369937 A1* | 12/2021 | Toth ....................... A61B 5/412 |

FOREIGN PATENT DOCUMENTS

| | | | |
|---|---|---|---|
| CN | 105652492 A | | 6/2016 |
| CN | 105852806 A | * | 8/2016 |
| CN | 106102322 A | | 11/2016 |
| DE | 102012211015 A1 | | 1/2014 |
| DE | 102013013013 A1 | | 2/2015 |
| EP | 2454990 A2 | | 5/2012 |
| EP | 2565630 A1 | | 3/2013 |
| EP | 3034054 A1 | | 6/2016 |
| EP | 3231478 A1 | | 10/2017 |
| EP | 3409190 A1 | | 12/2018 |
| EP | 3499510 A1 | | 6/2019 |
| EP | 3837520 A1 | | 6/2021 |
| GB | 1476894 A | | 6/1977 |
| GB | 2316171 A | | 2/1998 |
| GB | 2563602 A | | 12/2018 |
| JP | H05331438 A | | 12/1993 |
| JP | 2005231771 A | | 9/2005 |
| JP | 2009175150 A | | 8/2009 |
| JP | 2009225863 A | | 10/2009 |
| JP | 2010281580 A | | 12/2010 |
| KR | 20120119523 A | | 10/2012 |
| KR | 101224629 B1 | | 1/2013 |
| KR | 20140024743 A | | 3/2014 |
| KR | 20140058041 A | | 5/2014 |
| KR | 20160071044 A | | 6/2016 |
| KR | 20190105898 A | | 9/2019 |
| NL | 1027236 C2 | | 4/2006 |
| WO | WO-9731051 A1 | | 8/1997 |
| WO | WO-9839163 A2 | | 9/1998 |
| WO | WO-0021433 A1 | | 4/2000 |
| WO | WO-0043046 A2 | | 7/2000 |
| WO | WO-03067229 A1 | | 8/2003 |
| WO | WO-2006041997 A2 | | 4/2006 |
| WO | WO-2007030379 A2 | | 3/2007 |
| WO | WO-2008006150 A1 | | 1/2008 |
| WO | WO-2008010604 A1 | | 1/2008 |
| WO | WO-2009052607 A1 | | 4/2009 |
| WO | WO 2009/120951 A2 | | 10/2009 |
| WO | WO-2009141777 A1 | | 11/2009 |
| WO | WO-2010020919 A1 | | 2/2010 |
| WO | WO-2010105053 A2 | | 9/2010 |
| WO | WO-2011082420 A1 | | 7/2011 |
| WO | WO-2011113070 A1 | | 9/2011 |
| WO | WO-2011123848 A1 | | 10/2011 |
| WO | WO-2012141999 A1 | | 10/2012 |
| WO | WO-2013026999 A1 | | 2/2013 |
| WO | WO-2013044226 A2 | | 3/2013 |
| WO | WO-2014036577 A1 | | 3/2014 |
| WO | WO-2014116816 A1 | | 7/2014 |
| WO | WO-2015112095 A1 | | 7/2015 |
| WO | WO-2015168720 A1 | | 11/2015 |
| WO | WO-2016025438 A1 | | 2/2016 |
| WO | WO-2016030752 A1 | | 3/2016 |
| WO | WO-2016058032 A1 | | 4/2016 |
| WO | WO-2016073777 A1 | | 5/2016 |
| WO | WO-2016100218 A1 | | 6/2016 |
| WO | WO-2016109744 A1 | | 7/2016 |
| WO | WO-2016110564 A1 | | 7/2016 |
| WO | WO-2016187136 A1 | | 11/2016 |
| WO | WO-2016205872 A1 | | 12/2016 |
| WO | WO-2016205881 A1 | | 12/2016 |
| WO | WO-2017021006 A1 | | 2/2017 |
| WO | WO-2017021965 A2 | | 2/2017 |
| WO | WO-2017033058 A1 | | 3/2017 |
| WO | WO-2017037479 A1 | | 3/2017 |
| WO | WO-2017041014 A1 | | 3/2017 |
| WO | WO-2017041385 A1 | | 3/2017 |
| WO | WO-2017041386 A1 | | 3/2017 |
| WO | WO-2017041387 A1 | | 3/2017 |
| WO | WO-2017119996 A1 | | 7/2017 |
| WO | WO-2017205728 A1 | | 11/2017 |
| WO | WO-2017214188 A1 | | 12/2017 |
| WO | WO-2018035612 A1 | | 3/2018 |
| WO | WO-2018060417 A1 | | 4/2018 |
| WO | WO-2018064569 A1 | | 4/2018 |
| WO | WO-2018115461 A1 | | 6/2018 |
| WO | WO-2018144938 A1 | | 8/2018 |
| WO | WO-2018144941 A1 | | 8/2018 |
| WO | WO-2018144943 A1 | | 8/2018 |
| WO | WO-2018144946 A1 | | 8/2018 |
| WO | WO-2018162728 A2 | | 9/2018 |
| WO | WO-2018162732 A1 | | 9/2018 |
| WO | WO-2018162735 A1 | | 9/2018 |
| WO | WO-2018162736 A1 | | 9/2018 |
| WO | WO-2018185138 A1 | | 10/2018 |
| WO | WO-2018189265 A1 | | 10/2018 |
| WO | WO-2018209090 A1 | | 11/2018 |
| WO | WO-2018210692 A1 | | 11/2018 |
| WO | WO-2018210693 A1 | | 11/2018 |
| WO | WO-2018211458 A1 | | 11/2018 |
| WO | WO-2018234443 A1 | | 12/2018 |
| WO | WO-2019020550 A2 | | 1/2019 |

(56) References Cited

FOREIGN PATENT DOCUMENTS

| | | |
|---|---|---|
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A1 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020043806 A1 | 3/2020 |

OTHER PUBLICATIONS

"Qin, et al., Preparation and properties of polyurethane acrylates modified by saturated alcohols, 2013, Progress in Organic Coatings, 76, 1594-1599" (Year: 2013).*

Mehmood N., et al., "Applications of Modern Sensors and Wireless Technology In Effective Wound Management: Modern Sensors and Wireless Technology," Journal of Biomedical Materials Research Part B, vol. 102, May 1, 2014, XP055739544, pp. 885-895.

International Search Report and Written Opinion for Application No. PCT/EP2018/074176, dated Nov. 30, 2018, 15 pages.

Lu B., et al., "A Study of the Autofluorescence of Parylene Materials for µTAS Applications," Lab on Chip, vol. 10 (14), Jul. 2010, pp. 1826-1834.

Mostafalu P., et al., "Wireless Flexible Smart Bandage for Continuous Monitoring of Wound Oxygenation," IEEE Transactions on Biomedical Circuits and Systems, vol. 9 (5), Oct. 2015, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Preliminary Reporton Patentability for Application No. PCT/EP2018/074176, dated Mar. 19, 2020, 12 pages.

Jinto G., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Little Miss Plasters, kidstravelclub.co.uk., retrieved from http://www.kidstravelclub.co.uk/little-miss-girls-childrens-plasters on Aug. 26, 2016, 2 pages.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Adphox Corporation, "Corona discharge—Cause of Failure Lurking in a Power Switching Circuit", Japan, Retrieved from the Internet: URL: http://www.adphox.co.jp/technical/corona-failure-cause/, on Oct. 20, 2022, 22 pages.

* cited by examiner

500

500

Representation against colorless backdrop, without flourescence.

Representation against color backdrop, without flourescence.

Representation against color backdrop, with flourescence.

SYSTEMS AND METHODS FOR INSPECTION OF ENCAPSULATION AND COMPONENTS IN SENSOR EQUIPPED WOUND DRESSINGS

RELATED APPLICATIONS

This application is a U.S. national stage application of International Patent Application No. PCT/EP2018/074176, filed Sep. 7, 2018, which claims priority to U.S. Provisional Patent Application No. 62/556,479, filed on Sep. 10, 2017, which is hereby incorporated by reference in its entirety and made part of this disclosure.

BACKGROUND

Field

Embodiments of the present disclosure relate to apparatuses, systems, and methods for the treatment of tissues via sensor-enabled monitoring in communication with various therapy regimes.

Description of the Related Art

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

Many different types of wound dressings are known for aiding in the healing process of a human or animal. These different types of wound dressings include many different types of materials and layers, for example, gauze, pads, foam pads or multi-layer wound dressings. Topical negative pressure therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

However, prior art dressings for use in negative pressure wound therapy or other wound therapy provide little visualization or information of the condition of the wound site beneath the dressing. This can require the dressing to be changed prematurely before the desired level of wound healing has occurred or, for absorbent dressings, prior to the full absorbent capacity of the dressing being reached to allow the clinician to inspect the healing and status of the wound. Some current dressings have limited or unsatisfactory methods or features of providing information of conditions of the wound.

In some wound dressings, there may be a need to utilize electronic components within the wound and/or wound dressing. The electronic components of wound dressings and other devices may need to use coatings and/or adhesives and other encapsulation to protect the electronic components and/or patients. When coatings or adhesives are transparent, it can be difficult to determine if the electronic components are fully coated or that the coating and/or adhesive is appropriately applied. This can make it particularly difficult for medical devices to maintain biocompatibility.

SUMMARY

According to some embodiments, there is provided a method of inspection of a flexible printed circuit board, the method can comprise applying a coating material to the flexible printed circuit board, wherein the coating material comprises a material that will fluoresce when exposed to UV or visible light and the flexible printed circuit board comprises one or more electronic components and positioning the coated flexible printed circuit board under UV or visible light to cause the coating material to fluoresce.

The method of inspection of a flexible printed circuit board described in any of the preceding paragraphs may further comprise one or more of the following features. The coating material can comprise an adhesive material. The coating material can comprise an acrylated polyurethane. The method can further comprise displaying an image of the flexible printed circuit board under UV or visible light on a display. The image on the display can indicate location of the coating material. The image on the display can indicate location of the one or more electronic components and/or one or more electronic connections or tracks underneath the coating material. The UV or visible light can be transmitted from a light source on the same side of the flexible printed circuit board as a light sensor. The UV or visible light can be transmitted from a light source on an opposite side of the flexible printed circuit board from a light sensor. The method can further comprise measuring the intensity of fluorescence of the coating material while exposed to UV or visible light. The one or more electronic components can be visible under UV or visible light through the coating material. The method can further comprise positioning the flexible printed circuit board under UV light and under visible light. The method can further comprise displaying images of the flexible circuit board under different wavelengths of visible and/or UV light. The method can further comprise testing the flexible printed circuit board for a corona discharge. The method can further comprise taking an image of the location of the corona discharge.

According to some embodiments, there is provided a method of manufacturing a flexible sensor sheet for use on a wound, comprising providing a flexible substrate, positioning electronic components including one or more sensors for detecting wound characteristics on the flexible substrate, applying a coating material over the flexible substrate and/or the electronic components, and positioning the flexible substrate under UV or visible light to cause the coating material to fluoresce.

The method of manufacturing described in any of the preceding paragraphs may further comprise one or more of the following features. The coating material can comprise an adhesive material. The coating material can comprise an acrylated polyurethane. The method can further comprise displaying an image of the flexible substrate under UV or visible light on a display. The image on the display can indicate location of the coating material. The image on the display indicates location of the electronic components underneath the coating material. The the UV or visible light is transmitted from a light source on the same side of the flexible substrate as a light sensor. The UV or visible light is transmitted from a light source on an opposite side of the flexible printed circuit board from a light sensor. The method can further comprise measuring the intensity of fluorescence of the coating material while exposed to UV or visible light. The electronic components can be visible under UV or visible light through the coating material. The method can further comprise positioning the flexible substrate under UV light and under visible light. The method can further comprise displaying images of the flexible substrate under different wavelengths of visible and/or UV light. The method can further comprise testing the flexible printed circuit board for a corona discharge. The method can further comprise taking an image of the location of the corona discharge.

According to some embodiments, there is provided a flexible sensor sheet for use on a wound. The flexible sensor sheet can comprise a flexible substrate, electronic components including one or more sensors positioned on the flexible substrate for detecting wound characteristics, and a material that will fluoresce when exposed to UV or visible light coating the flexible substrate and/or electronic components.

In some embodiments, the flexible sensor sheet described in any of the preceding paragraphs can include one or more of the following features. The material that will fluoresce when exposed to UV or visible light can comprise an adhesive material. The material that will fluoresce when exposed to UV or visible light can comprise an acrylated polyurethane. A first portion of the flexible substrate can be coated with a first material that will fluoresce when exposed to UV or visible light and a second portion of the flexible substrate can be coated with a second material that will fluoresce when exposed to UV or visible light, wherein the first material can be different than the second material.

According to some embodiments, there is provided a method of inspection of a flexible printed circuit board or a flexible sensor sheet, the method can comprise testing the flexible printed circuit board for a corona discharge.

According to some embodiments, there is provided a method of inspection of a flexible printed circuit board, the method can comprise applying a coating material to the flexible printed circuit board, wherein the coating material comprises a material configured to fluoresce when exposed to a UV or visible light and the flexible printed circuit board comprises one or more electronic components, positioning the coated flexible printed circuit board under UV or visible light to cause the coating material to fluoresce, measuring a fluorescence emission of the coating material to detect void spaces or uneven application of the coating material, and measuring an optical transmission of the coating material to detect gas bubbles in the coating material.

The method described in any of the preceding paragraphs may further comprise one or more of the following features. A wound facing surface of the flexible printed circuit board cab be exposed to UV or visible light. A side opposite a wound facing surface of the flexible printed circuit board can be exposed to UV or visible light. The coating material can comprise an adhesive material. The coating material can comprise an acrylated polyurethane. The method can further comprise displaying an image of the flexible printed circuit board under UV or visible light on a display. The image on the display can indicate location of the coating material. The image on the display can indicate location of the one or more electronic components underneath the coating material. The UV or visible light can be transmitted from a light source on the same side of the flexible printed circuit board as a light sensor. The UV or visible light can be transmitted from a light source on an opposite side of the flexible printed circuit board from a light sensor. The method can further comprise measuring the intensity of fluorescence of the coating material while exposed to UV or visible light. The one or more electronic components can be visible under UV or visible light through the coating material. The method can further comprise positioning the flexible printed circuit board under UV light and under visible light. The method can further comprise displaying images of the flexible printed circuit board under different wavelengths of visible and/or UV light. The method can further comprise testing the flexible printed circuit board for a corona discharge. The method can further comprise taking an image of the location of the corona discharge.

According to some embodiments, there is provided a method of inspection of an extensible and flexible printed circuit board, the method can comprise applying a coating material to the extensible and flexible printed circuit board, wherein the coating material comprises a material that will fluoresce when exposed to UV or visible light and the extensible and flexible printed circuit board comprises one or more electronic components, and positioning the coated extensible and flexible printed circuit board under UV or visible light to cause the coating material to fluoresce.

Other embodiments of a wound dressing, devices, kits and associated methods are described below.

BRIEF DESCRIPTION OF THE DRAWINGS

Embodiments of the present disclosure will now be described hereinafter, by way of example only, with reference to the accompanying drawings in which.

DETAILED DESCRIPTION

Figure 1:
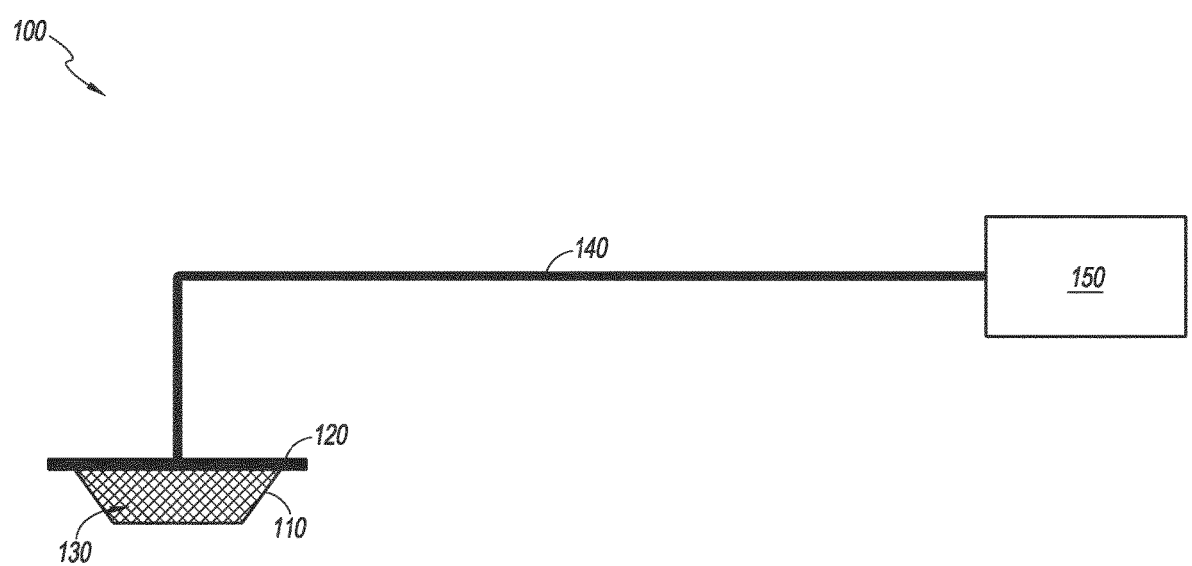
FIG. 1 illustrates a negative pressure wound treatment system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:

an absorbent layer for absorbing wound exudate and an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film Typically, the translucent film has a moisture vapour permeability of 500 g/m2/24 hours or more.

The translucent film may be a bacterial bather.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm2.

The support layer may have a tensile strength from 0.05 to 0.06 Nm.

The support layer may have a thickness of from 50 to 150 μm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 µm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

Wound Therapy System Overview

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover 120 by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. In some embodiments, fluid is absorbed by the wound filler 130 or one or more absorbent layers (not shown).

Wound Dressing Overview

Figure 2:
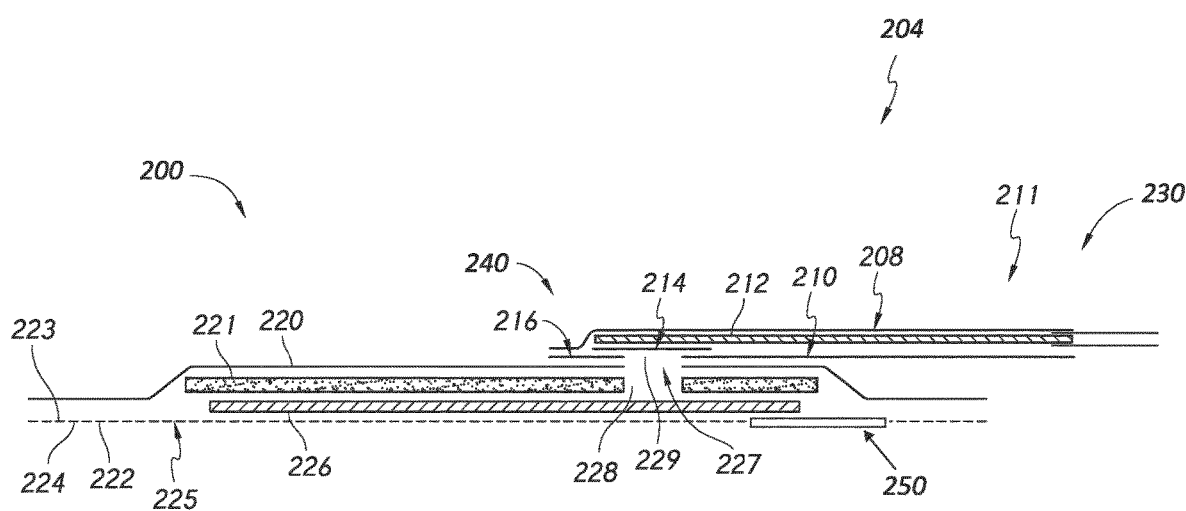
FIG. 2 illustrates a wound dressing and a fluidic connector according to some embodiments.

FIG. 2 illustrates a cross-section view of a wound dressing 200, which can be similar to or the same as the wound cover 120 and the wound filler 130 of FIG. 1, with a fluidic connector 204, which can be similar to or the same as the conduit 140 of FIG. 1. The wound dressing 200 can include a top or cover layer, or backing layer 220 attached to a wound contact layer 222, which can be joined or sealed together so as to define an interior space or chamber. This interior space or chamber may comprise additional structures that may be adapted to distribute or transmit negative pressure, store wound exudate and other fluids removed from the wound, and other functions. Examples of such structures include a transmission layer 226 and an absorbent layer 221 described herein. Moreover, one or more sensors 250, which can be part of a sensor array, can be incorporated onto or into the wound dressing 200, such as the wound contact layer 222 as illustrated.

As used herein the upper layer, top layer, or layer above refers to a layer farthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 has a lower surface 224 (for example, facing the wound) and an upper surface 223 (for example, facing away from the wound). The perforations 225 can comprise through holes in the wound contact layer 222 which enable fluid to flow through the wound contact layer 222. The wound contact layer 222 helps prevent tissue ingrowth into the other material of the wound dressing 200.

A porous layer 226 of porous material can be located above the wound contact layer 222. This porous layer, or transmission layer, 226 allows transmission of fluid including liquid and gas away from a wound site into upper layers of the wound dressing 200. In particular, the transmission layer 226 can ensure that an open air channel can be maintained to communicate negative pressure over the wound area even when the absorbent layer has absorbed substantial amounts of exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

An aperture, hole, or orifice 227 is provided in the backing layer 220 to allow a negative pressure to be applied to the wound dressing 200. The fluidic connector 204 can be attached or sealed to the top of the backing layer 220 over the orifice 227 made into the wound dressing 200, and communicates negative pressure through the orifice 227.

In some embodiments, the absorbent layer 221 includes at least one through hole 228 located so as to underlie the fluidic connector 204. The through hole 228 may be the same size as the opening 227 in the backing layer, or may be bigger or smaller. The aperture or through-hole 228 can be provided in the absorbent layer 221 beneath the orifice 227 such that the orifice is connected directly to the transmission layer 226. This allows the negative pressure applied to the fluidic connector 204 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided.

Turning now to the fluidic connector 204, some embodiments include a sealing surface 216, a bridge 211 with a proximal end 230 and a distal end 240, and a filter 214. The sealing surface 216 can form the applicator previously described that is sealed to the top surface of the wound dressing 200. A bottom layer of the fluidic connector 204 may include the sealing surface 216. The fluidic connector 204 may further comprise an upper surface vertically spaced from the sealing surface 216, which in some embodiments is defined by a separate upper layer of the fluidic connector 204. In other embodiments the upper surface and the lower surface may be formed from the same piece of material. In some embodiments the sealing surface 216 may comprise at least one aperture 229 therein to communicate with the wound dressing 200.

The bridge 211 may include a first fluid passage 212 in communication with a source of negative pressure, the first fluid passage 212 comprising a porous material, such as a 3D knitted material, which may be the same or different than the porous layer 226. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge Sensor-Enabled Wound Dressings A wound dressing, such as the wound dressing 200 of FIG. 2, can incorporate a number of sensors or sensors, such as the one or more sensors 250 of FIG. 2. A number of sensor technologies can be used in wound dressings or one or more components forming part of an overall wound dressing apparatus. For example, one or more sensors can be incorporated onto or into a wound contact layer or sheet, such as the wound contact layer 222 of FIG. 2, that can be placed in contact with the wound and allow fluid to pass through while causing little to no damage to the tissue in the wound. The sensor-integrated wound contact layer or sheet can be made of a flexible material such as silicone and can incorporate antimicrobials or other therapeutic agents. The sensor-integrated wound contact layer or sheet can incorporate adhesives that adhere to wet or dry tissue. In yet other implementations, the one or more sensors can additionally or alternatively be incorporated into or encapsulated within other components of the wound dressing, such as the absorbent layer or spacer layer.

In some implementations, the one or more sensors can include sensors for monitoring temperature (such as, 25 thermistor sensors, in a 5×5 array, ~20 mm pitch), pulse oximetry or SpO2 (such as, 4 or 5 SpO2 sensors, in a single line from the center of the wound contact layer to the edge thereof, 10 mm pitch), optical properties of the tissue, exudate, or foreign bodies (such as, 10 optical sensors, in 2×5 array, ~20 mm pitch; not all 5 sensors in each row of the array need be aligned), pH (such as, by measuring colour of a pH sensitive pad, optionally using the same optical sensors as for tissue colour), and impedance (such as, 9 impedance contacts, in a 3×3 array, ~40 mm pitch). Other sensors, such as pressure, flow, strain, colorimetric sensors configured to measure biological or chemical compounds (for example, dye coated colorimetric sensors) or the like, can be additionally or alternatively used. Colorimetric sensors can be used for measure odor, toxicity, etc. Any one or more sensors described herein can be placed or positioned to obtain measurements of any location in the wound or the skin.

The sensors can be supported by or incorporated onto a flexible or substantially flexible substrate, such as one or more of flexible or substantially flexible printed circuits (FPCs) which can be formed from flexible polymers including polyamide, polyimide (PI), polyester, polyethylene naphthalate (PEN), polyetherimide (PEI), polyurethane, thermoplastic polyurethane (TPU), along with various fluropolymers (FEP) and copolymers, or any other suitable material. Substantially flexible or flexible substrates can include single-sided, double-sided, or multi-layer circuits. In some implementations, the sensor array can be incorporated into a two-layer flexible circuit. In some embodiments, the FPC can be a multi-layer flexible printed circuit. In some embodiments, these flexible printed circuits can be incorporated into any layer of the wound dressing. In some embodiments, a flexible circuit can be incorporated into (for example, positioned on or in) a wound contact layer. For example, the flexible circuit can be incorporated into a wound contact layer similar to the wound contact layer described with reference to FIG. 2. The wound contact layer can have cutouts or slits that allow for one or more sensors to protrude out of the lower surface of the wound contact layer and contact the wound area directly.

The sensor-integrated wound contact layer can include a first and second wound contact layer with an FPC sandwiched between the two layers of wound contact layer material. The first wound contact layer has a lower surface intended to be in contact with the wound and an upper surface intended to be in contact with the FPC. The second wound contact layer has a lower surface intended to be in contact with the FPC and an upper surface intended to be in contact with a wound dressing or one or more components forming part of an overall wound dressing apparatus. The upper surface of the first wound contact layer and the lower surface of the second wound contact layer can be adhered together with the FPC sandwiched between the two layers.

Figure 3A:
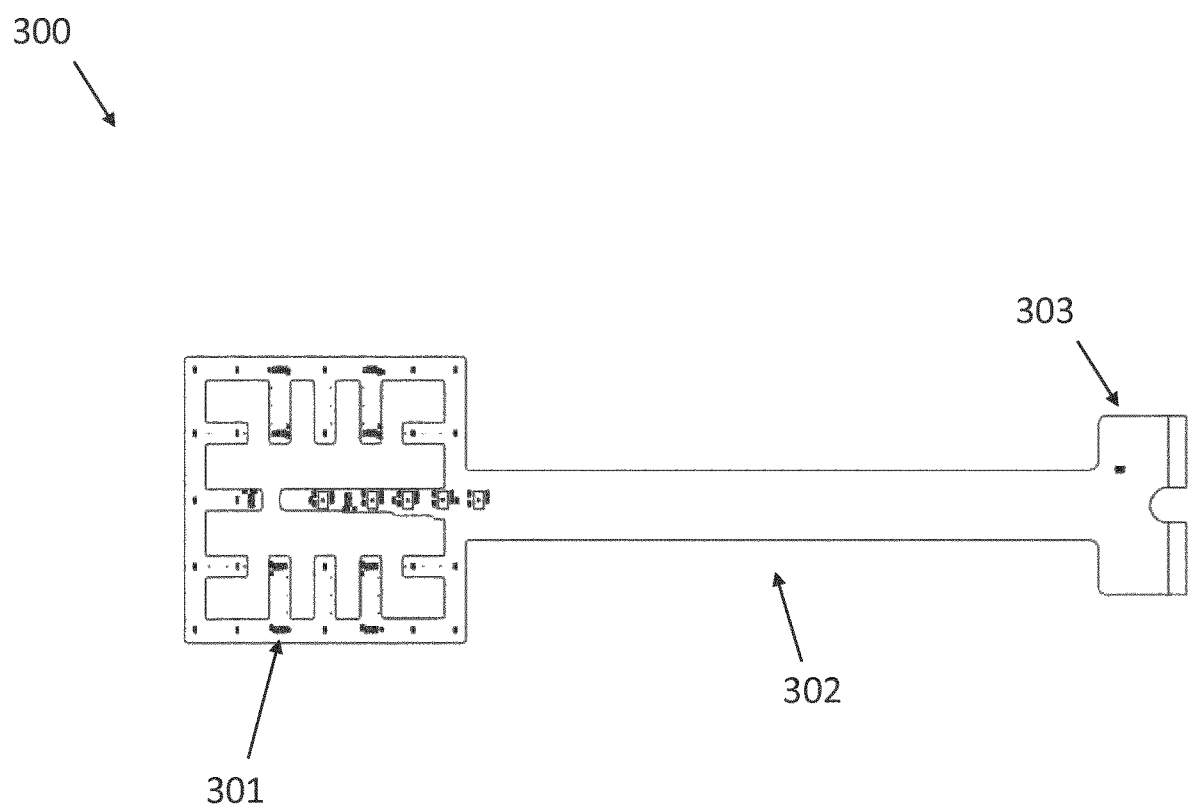
FIG. 3A illustrates a sensor array that may be incorporated into a wound dressing according to some embodiments.

FIG. 3A illustrates a sensor array 300 including a sensor portion 301, a tail portion 302, and a connector pad end portion 303. The sensor portion 301 can include one or more of a temperature sensor, impedance sensor, optical sensor, and SpO2 sensor, among other possible sensors, as well as associated circuitry. The sensor array 300 can be a flexible sensor array printed circuit. The tail portion 302 can extend from the sensor portion 301 to the connector pad end portion 303. The connector pad end portion 303 can electrically or electronically connect to a control module or other processing unit to receive the data from the sensor portion 301. The sensor array 300 can be incorporated onto or into a wound dressing like the wound dressing 200 of FIG. 2, such as in the wound contact layer 222 of the wound dressing 200.

Figure 3B:
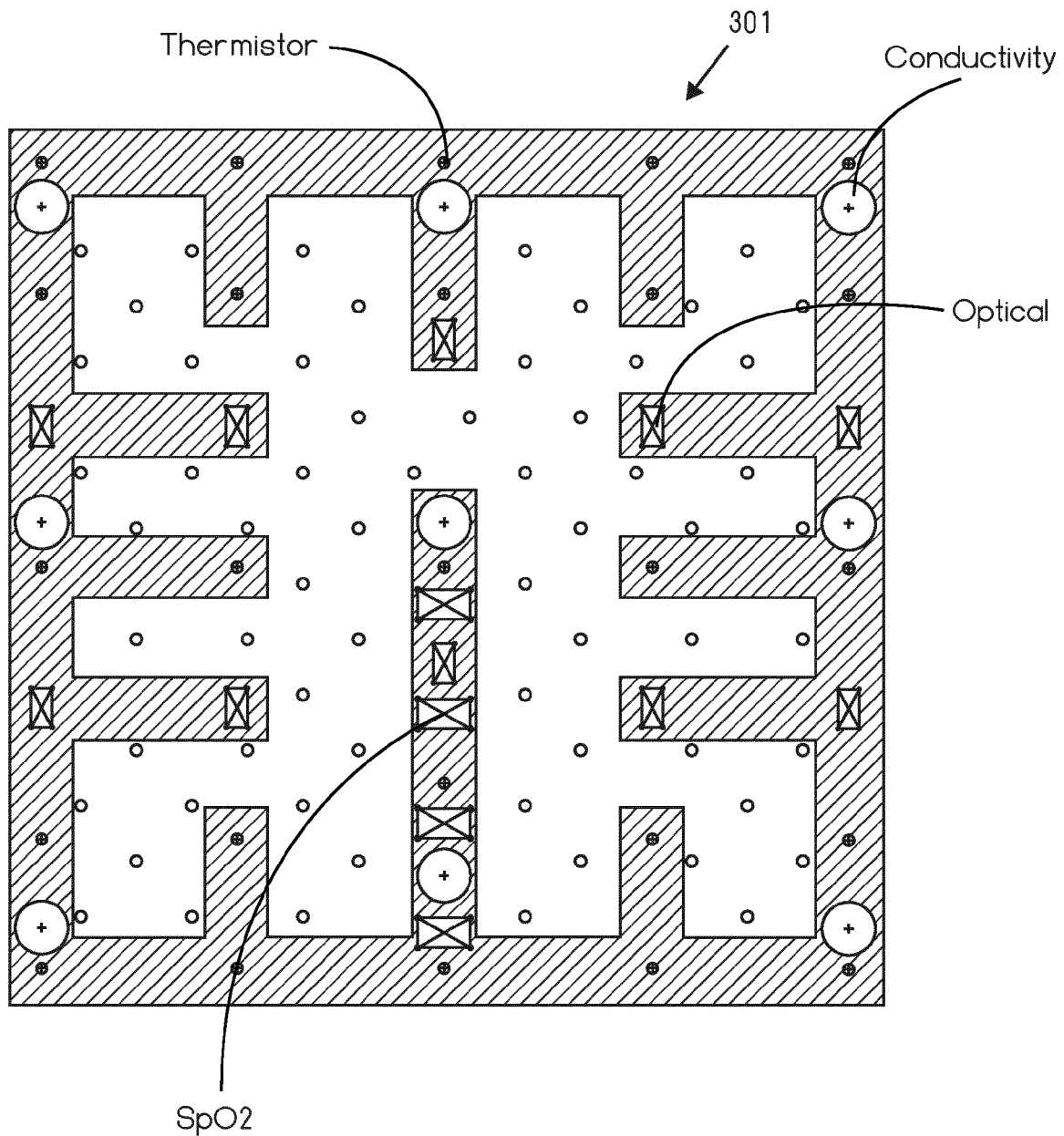
FIG. 3B illustrates a sensor portion of a sensor array according to some embodiments.

FIG. 3B illustrates the sensor portion 301 of the sensor array 300 of FIG. 3A according to some embodiments. The sensor portion 301 can include a plurality of portions that extend either around a perimeter of a wound dressing component such as a wound contact layer, or inward from an outer edge of the wound dressing component. For example, the embodiment illustrated in FIG. 3B includes a plurality of linearly extending portions that may be parallel to edges of a wound dressing component, and in some embodiments, follow the entire perimeter of the wound dressing component. In some embodiments, the sensor portion 301 may comprise a first plurality of parallel linearly extending portions that are perpendicular to a second plurality of parallel linearly extending portions. These linearly extending portions may also have different lengths and may extend inward to different locations within an interior of a wound dressing component. In some embodiments, the sensor portion 301 does not cover the entire wound dressing component, so that gaps are formed between portions of the sensor array 300.

As can be seen from FIG. 3B, one or more temperature sensors, impedance sensors (or conductivity sensors), SpO2 sensors, or optical, ultraviolet (UV), infrared (IR), or other type of visible or invisible light sensors can be used on the sensor array to provide information relating to conditions of the wound. Optical, ultraviolet (UV), infrared (IR), or other type of visible or invisible light or other electromagnetic spectrum sensors can provide spectral measurement(s) of the wound. The one or more sensors can assist a clinician in monitoring the healing of the wound and operate individually or in coordination with each other to provide data relating to the wound and wound healing characteristics.

An impedance sensor can be, for example, used to determine the difference between living and dead tissue or to show a change in impedance due to a wound being opened up in morbid tissue. The impedance sensors can include Ag/AgCl electrodes and an impedance analyzer. The impedance sensor can, for instance, be used to measure the change of impedance of a region of wound growth by measuring the impedance of the surrounding tissue/area. The impedance sensor can be used in the wound bed or on the perimeter of the wound or may be used to detect adherence failure of the dressing.

The sensor portion 301 can, in some implementations, utilize impedance sensors to measure the change in impedance on perimeter electrodes due to a wound size or wound shape change. For example, tomographic reconstruction or techniques can be used to infer wound size by using different spacing of impedance sensors or electrodes. Voltage or current probes can be used to apply voltage or current stimuli to determine or test patient's nerve responses or to promote wound healing. Impedance can be measured through a conductive path that goes through a biocompatible layer (for example, of the wound dressing) or through a biocompatible gel layer (for example, conductive gel layer) or saline solution to contact the wound. Measurements can be made in a frequency range of about 2.5 kHz to about 100 kHz. This can be similar to using large patch clamp measurements.

Alternatively or additionally, impedance can be measured using capacitance or a capacitive-coupling method without forming direct contact with the tissue (for example, using non-contact electrodes). For example, transmission in the frequency range of about 30 kHz to about 70 kHz can be used. Impedance can be measured using three point probe measurement or four point probe measurement. Impedance of one or more of wound tissue or exudate can be measured, which can be used to infer cell or tissue health. Impedance of a region around a wound (such as, skin or tissue surrounding the wound) can be measured. Impedance sensors can be retractable to move in out as needed. Impedance sensors can include fine or micro probe needles with conductive tips which extend into the wound and insulating shafts. The impedance sensor can be dangling probes under a wound contact layer, which come into contact with the wound. The impedance sensor can include dry contact electrodes. The impedance sensors can include electrodes, such as gold, silver, platinum, or carbon electrodes, that ensure or promote biocompatibility.

In certain implementations, a controller (such as a microprocessor) can be mounted on the wound dressing and connected to the one or more sensors. Such a mounted controller can communicate with a control module over a connection, such as 3 or 4 wire connection (or less or more wires), to alleviate burdens associated with connecting to external component(s). For example, the tail portion 302 can include a 3 or 4 wire connection. In some implementations, the mounted controller can communicate wirelessly.

The controller or control module can be used to interface with the sensor array 300. The control module can contain a power source, such as batteries, and electronics to drive the sensors. The control module can also log data at appropriate intervals and allow data transfer to an external computing device, such as a personal computer (PC). The control module can be customized to have various features depending on the sensors used in the sensor array 300 and the data collected by the sensors. The control module can be comfortable enough and small enough to be worn continuously for several weeks and may be positioned near the wound dressing or on the wound dressing. In some embodiments, the control module can be positioned in a remote location from the wound dressing and accompanying sensor array 300. The control module can communicate with the sensor array 300 and wound dressing through electrical wires or through wireless communication whether positioned on the dressing, near the dressing, or remote from the wound dressing. The control module, in some implementations, can determine a characteristic of the wound from the data collected by the sensor array 300 and activate an alarm responsive to the characteristic, such as to indicate the dead tissue is detected.

The control module can include various requirements and combination of features including but not limited to the features listed in Table 1 below.

TABLE 1

| OPTIONAL FEATURES FOR CONTROL MODULE |
| --- |
| 7 day operation from a single set of batteries |
| 28 day local, non-volatile, storage capacity |
| Easy to charge, or to replace battery |
| Wireless link to PC/tablet (such as Bluetooth) |
| Wired link to PC (optional, micro-USB) |
| Drive electronics for temperature sensors (such as, thermistors) |
| Drive electronics for impedance sensors |
| Drive electronics for optical sensors |
| Drive electronics for SpO2 sensors |
| Power management |
| Real Time Clock (RTC) to allow accurate data logging, and correlation with other measurands |
| Ability to change sample rates and intervals (useful for SpO2) for each sensor |
| Indication of status visually, audibly, tangibly, or the like. For example, via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low |

Figure 3C:
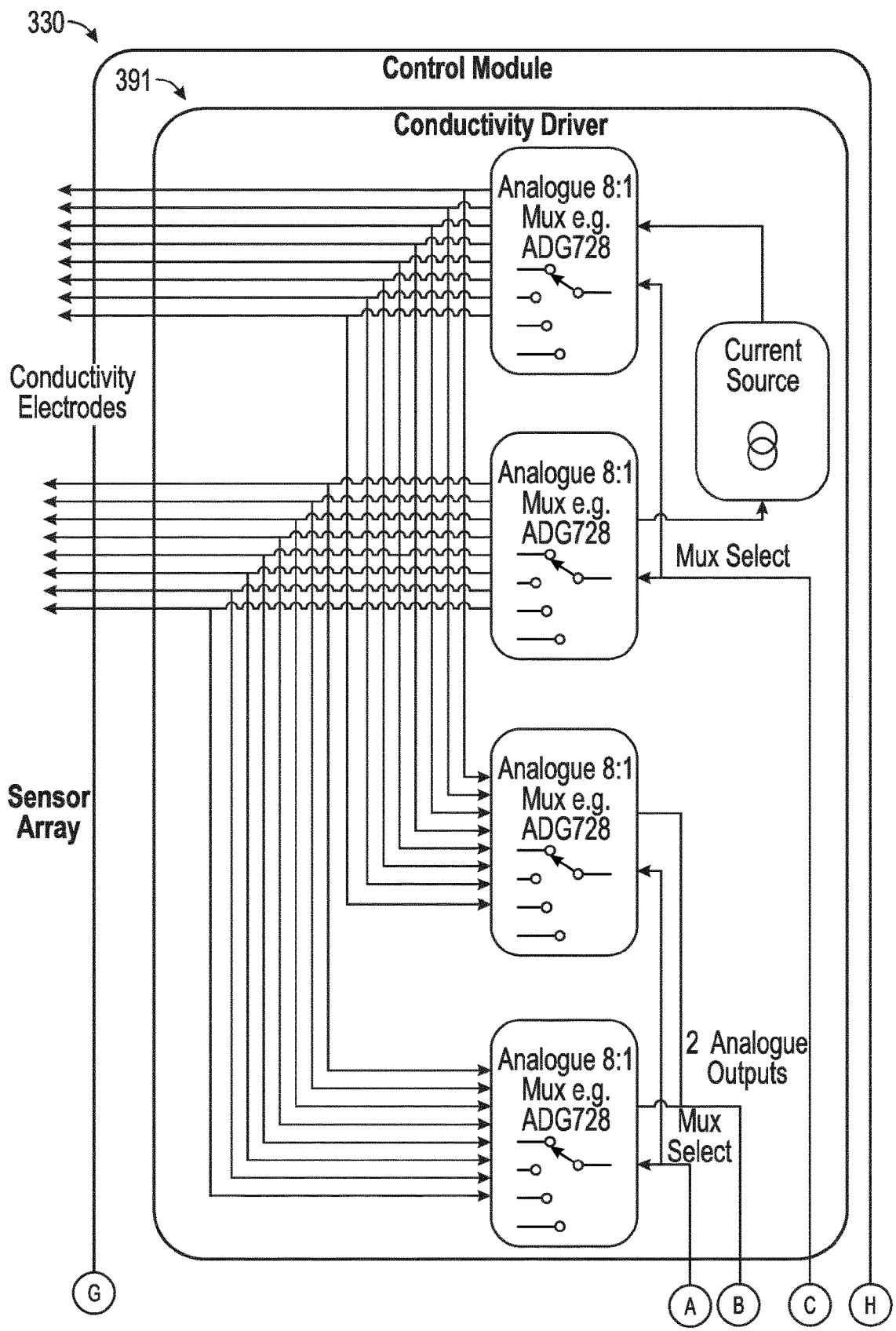
FIG. 3C illustrates a control module according to some embodiments.
Figure 3C:
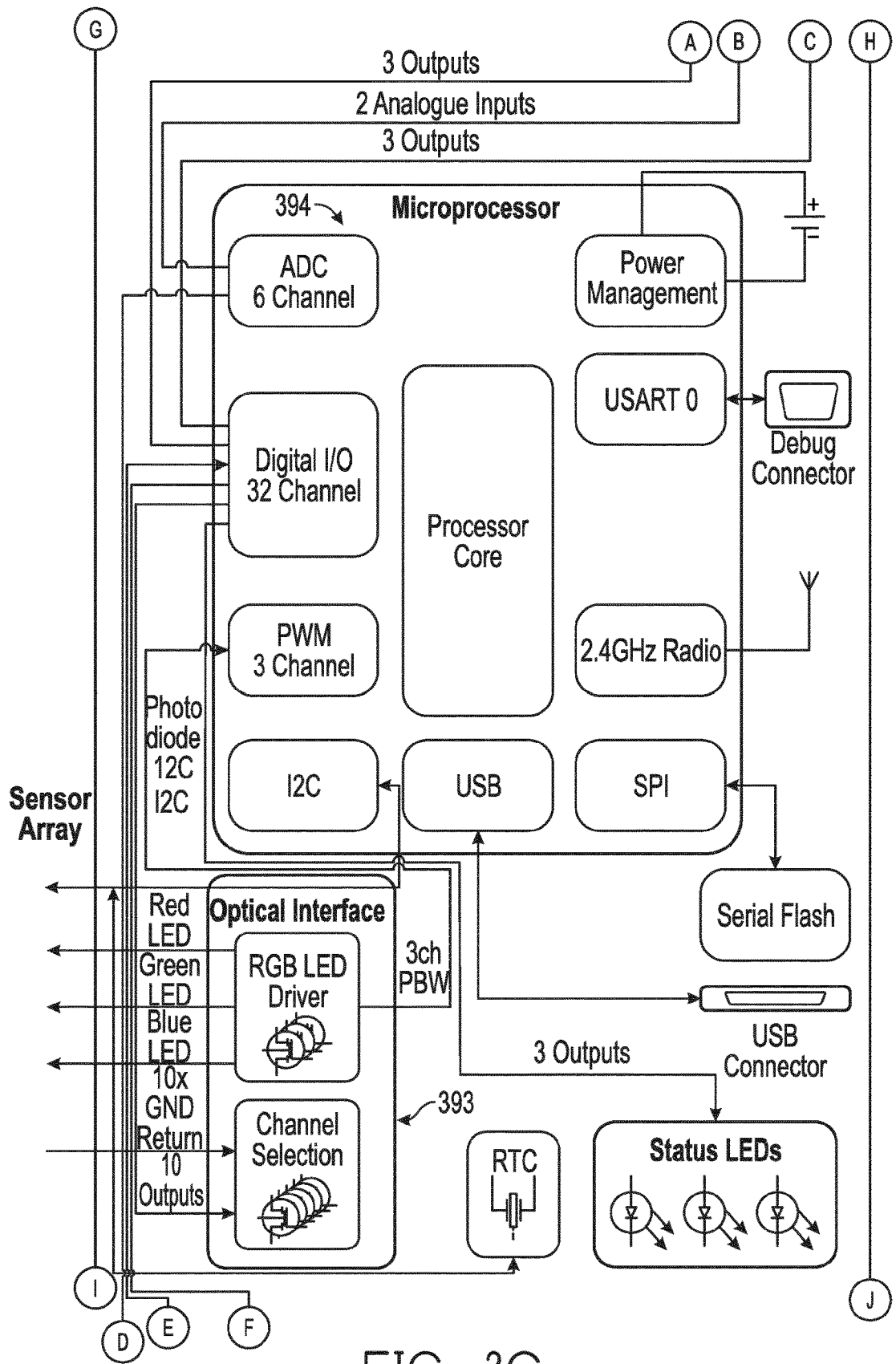
Figure 3C:
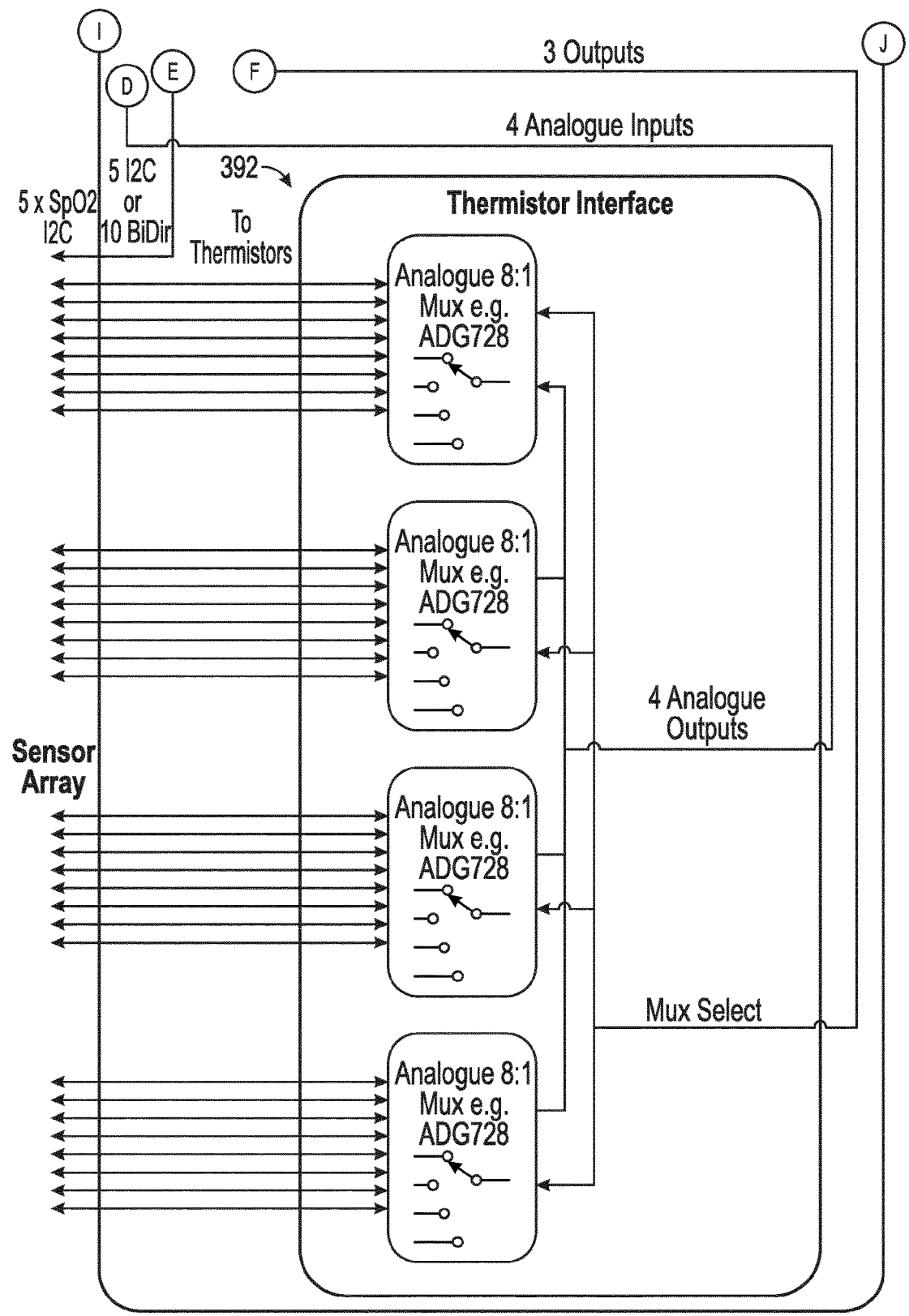

FIG. 3C illustrates a block diagram of a control module 390 according to some embodiments. The control module 390 includes an impedance driver box 391 supporting features of an impedance driver. Box 392 supports the features of the temperature sensor (for example, thermistor) interface, and box 393 supports the features of the optical interface. The control module 390 can include a controller or microprocessor 394 with features including a Real time clock (RTC), Status LEDs, USB connector, Serial Flash, and Debug Connector.

The control module can include a memory component where the amount of local storage depends on the sample rate and resolution of the sensors. The control module can utilize one or more analogue switches. The control module can incorporate a power source, such as a battery, or may instead utilize a power source separate from the control module. The control module can incorporate a real time clock (RTC). The printed circuit board (PCB) of the control module can be a 4-layer board, approximately 50 mm×20 mm, or 25 mm×40 mm. The type of PCB used can be largely driven by connection requirements to sensor array.

The data collected through the sensor array can be passed through the control module and processed by a host software. The software may be executed on a processing device. The processing device can be a PC, tablet format computing device or a tablet, smartphone, or other computer capable of running host software (for example, a custom made computing device). The processing device executing the software can be in communication with the control module through electrical wires or through wireless communication.

Electronics, including one or more of sensors or control module, can be constructed to be compatible or safe for x-ray, MRI, or other type of scanning. Electronics can be constructed to be compatible or safe with external or implantable defibrillators. Electronics can include protection against radiofrequency interference (RFI) or electromagnetic interference (EMI). For example, one or more EMI shields can be used, which can be made out of ferrite, copper, or another material. Faraday cages, or the like.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

Component Positioning

In some embodiments, electrical or electronic components, such as sensors, connections, or the like, can be placed or positioned on or embedded in one or more wound dressing components, which can be placed in or on the wound, skin, or both the wound and the skin. For example, one or more electronic components can be positioned on a wound contact layer side that faces the wound, such as the lower surface 224 of the wound contact layer 222 in FIG. 2. The wound contact layer can be flexible, elastic, or stretchable or substantially flexible, elastic, or stretchable in order to conform to or cover the wound. For example, the wound contact layer can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material. In some instances, one or more electronic components can be alternatively or additionally placed or positioned on or embedded in any one or more of a transmission layer, absorbent layer, backing layer, or any other suitable layer of the wound dressing.

In some implementations, while it may be desirable for the wound contact layer to be stretchable to better conform to or cover the wound, at least some of the electronic components may not be stretchable or flexible. In such instances, undesirable or excessive localized strain or stress may be exerted on the one or more electronic components, such as on the supporting area or mountings of an electronic component, when the wound is dressed with the wound dressing and the wound contact layer is positioned in or over the wound. For example, such stress can be due to patient movement, changes in the shape or size of the wound (such as, due to its healing), or the like. Such stress may cause movement, dislodgment, or malfunction of the one or more electronic components (for example, creation of an open circuit from a pin or another connector becoming disconnected). Alternatively or additionally, it may be desirable to maintain the position of one or more electronic components, such as one or more sensors, in the same or substantially same location or region on the wound contact layer with respect to the wound (such as, in contact with the wound) so that measurements collected by the one or more electronic components accurately capture changes over time in the same or substantially same location or region of the wound. While the surface of the stretchable wound contact layer may move when, for example, the patient moves, it may be desirable to have the one or more electronic components be located in the same location or region with respect to the wound.

As described herein, in some embodiments, one or more stiff, rigid, or non-stretchable or substantially stiff, rigid, or non-stretchable regions, such as one or more regions of non-stretchable or substantially non-stretchable material, can be mounted, positioned, or placed on the wound contact layer (or another suitable wound dressing component) for supporting one or more electronic components. Mounting, positioning, or placing one or more electronic components in the one or more non-stretchable or substantially non-stretchable regions can prevent formation of localized stress or assist with maintenance of the position of the one or more electronic components with respect to the wound. In some instances, one or more electronic components can be alternatively or additionally flexible, such as mounted or printed on or supported by one or more flexible materials. For example, flexible plastic sheets or substrates, such as polyimide, polyether ether ketone (PEEK), polyester, silicone, or the like, can be used.

Figure 4A:
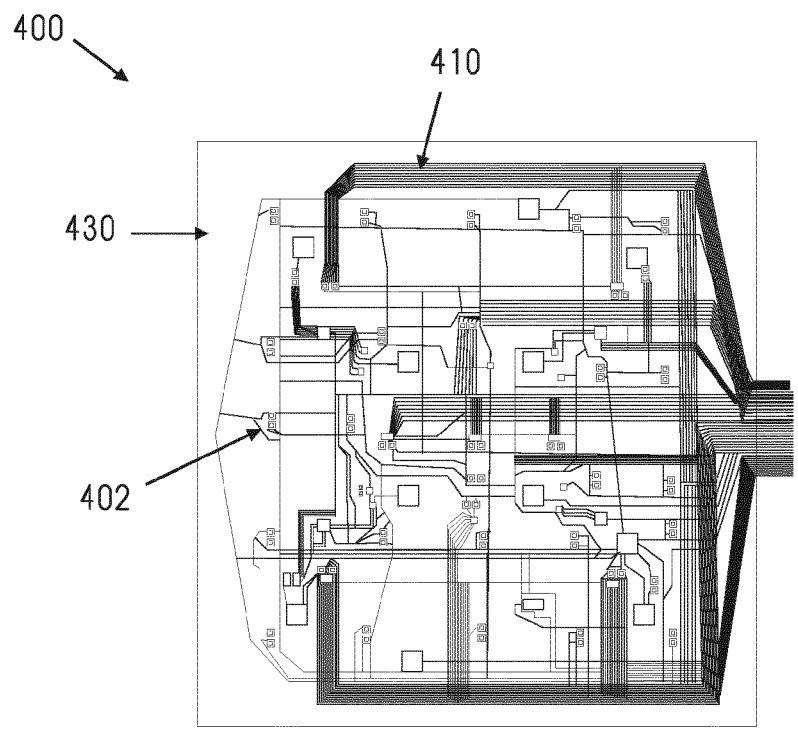
FIGS. 4A-4B illustrate a component for use in a wound dressing with a plurality of electronic components according to some embodiments.
Figure 4B:
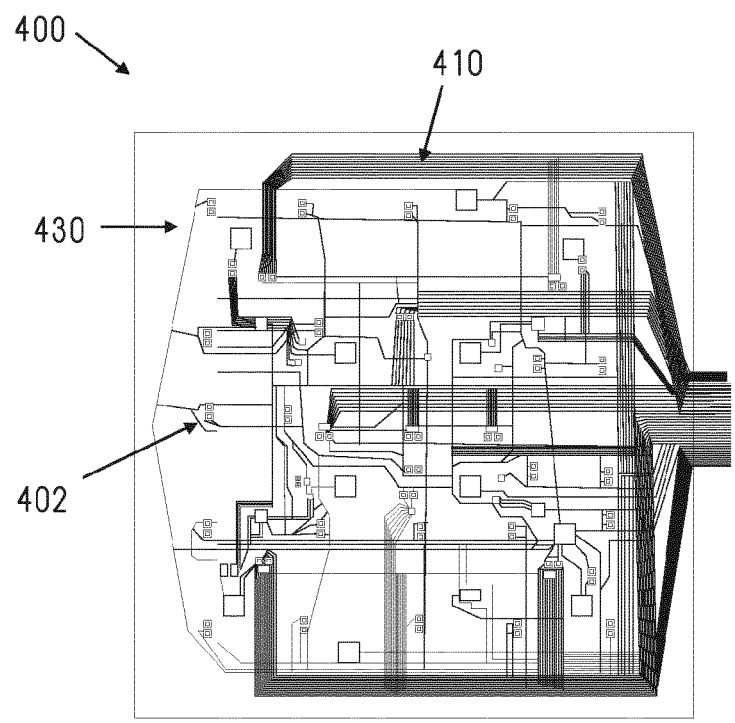

FIGS. 4A-4B illustrate a component 400 with a plurality of electronic components according to some embodiments. As is shown, a sheet or substrate 430 is configured to support one or more electronic components, including an electronic component or module 402 with a plurality of connectors and a plurality of electronic connections 410, and non-stretchable or substantially non-stretchable regions. The substrate 430 can be a stretchable or substantially stretchable wound contact layer and can be used with a wound dressing apparatus as described herein.

The electronic module 402 can be any electronic component described herein, such as a sensor, light source (such as an LED, temperature sensor, optical sensor, etc.), controller or processor (such as a communication processor), or the like.

Electronic connections 410 can be tracks printed on the substrate 430, such as using conductive copper, conductive ink (such as silver ink, graphite ink, etc.), or the like. At least some of the electronic connections can be flexible or stretchable or substantially flexible or stretchable and can connect the components or module 402 to the electronic connections 410.

Connectors can be configured to electronically connect the electronic module 402 to the electronic connection 410 (as illustrated in FIG. 4B), which in turn can be connected to other electronic modules (not shown) positioned on the substrate 430, on or in other components of the wound dressing, or external to the wound dressing. Connectors can be pins, leads, bumps, or the like. Additionally or alternatively a socket can be used to support and electronically connect the electronic module 402.

Regions of the substrate or sheet 430 can include non-stretchable or substantially non-stretchable material, such as one or more of suitable adhesive, epoxy, polyester, polyimide, polyamide, PET, PBT, or another type of material with a high Young's modulus. One or more of the regions of the non-stretchable or substantially non-stretchable material can be printed on the substrate 430. As is used herein, printing material on a substrate can include one or more of laminating, adhering, or any other suitable technique.

As described herein, the components of the sheet 430 can be positioned in certain predefined configurations. It can be desirable to inspect and confirm positioning of the components of the sheet 430. Component indexing can be used to automatically locate position of the one or more components on the substrate so that proper positioning of the one or more components and be confirmed.

Component Encapsulation

One or more of coating or one or more adhesive regions can be applied to one or more components or regions of the sheet 430 according to some embodiments. In some embodiments, the coating can be a conformal coating configured to encapsulate or coat one or more of the substrate or sheet 430 or components supported by the substrate, such as the electronic connections 410 or the electronic module 402. The coating can provide biocompatibility, shield or protect the electronics from coming into contact with fluids, or the like. The coating can be one or more of a suitable polymer, adhesive, such as 1072-M UV, light, or thermal curable or cured adhesive, Optimax adhesive (such as, NovaChem Optimax 8002-LV), parylene (such as, Parylene C), silicon, epoxy, urethane, acrylated urethane, silicone, or another suitable biocompatible and stretchable material.

In some embodiments, the coating can be thin, such as about 100 microns thick, less than about 100 microns thick, or more than about 100 microns thick. The coating can be applied and cured using one or more of UV, light, or thermal curing. In some implementations, the coating can be applied on the other side of the substrate 430 (or side facing away from the wound) particularly if the substrate is not impermeable to fluid.

In some embodiments, one or more adhesive pads, tracks, or regions can be applied to the wound facing side of the substrate 430. In some embodiments, one or more adhesive regions can be patterned to position or affix specific components in particular areas, regions, or locations in contact with or relative to the wound even while the substrate 430 is under stress or strain.

In some embodiments, the pattern of the adhesive regions can be based on the positioning of the one or more electronic components, which can be determined using indexing as described herein. In some embodiments, it may be desirable to pattern the adhesive to equalize the stress or strain on the wound contact layer.

The adhesive can be patterned to strengthen or support certain areas or regions, such as regions where one or more electronic components are placed, while weakening (or making less rigid) other regions to distribute the stress or to avoid straining the one or more electrical components. For example, it may be desirable to cover at least 50% or more of the wound facing surface of the wound contact layer with the adhesive. In certain implementations, adhesive can be applied to cover or substantially cover the entire wound facing side of the wound contact layer.

A coating can be applied to the sheet 403 or electronic components positioned on the sheet 403. In some embodiments, the coating can be a biocompatible coating. In some embodiments, the sheet 403 can be a wound contact layer including a thin, flexible substrate that conforms to the wound. For example, the substrate or sheet can be made from stretchable or substantially stretchable material or film, such as polyurethane, TPU, silicone, polycarbonate, polyethylene, polyimide, polyamide, polyester, PET, PBT, PEN, PEI, along with various FEP and copolymers, or another suitable material. The substrate may not be biocompatible. The coating can be flexible. The coating can include one or more suitable polymers, adhesives, such as 1072-M adhesive (for example Dymax 1072-M), 1165-M adhesive (such as, NovaChem Optimax 8002-LV, Dymax 1165-M, or the like), 10901-M adhesive (for instance, Dymax 1901-M or 9001-E Dymax), parylene (such as, Parylene C), silicones, epoxies, urethanes, acrylated urethanes, acrylated urethane alternatives (such as, Henkel Loctite 3381), or other suitable biocompatible and substantially stretchable materials. Coating can be thin coating, for example, from about 80 microns or less up to several millimeters or more. As described herein, coating can be applied by laminating, adhering, welding (for instance, ultrasonic welding), curing by one or more of light, UV, heat, or the like. Coating can be transparent or substantially transparent to permit optical detection. Coating can retain bond strength when subjected to sterilization, such as EtO sterilization. Coating can have hardness lower than about A100, A80, A50 or lower. Coating can have elongation at break higher than about 100%, 200%, 300% or more. Coating can have viscosity of about 8,000-14,500 centipoise (cP). In some cases, coating can have viscosity no less than about 3,000 cP. In some cases, coating can have viscosity less than about 3,000 cP. Coating can be fluorescent.

The coating can be a thin coating, for example, from about 80 microns or less up to several millimeters or more. As described herein, coating can be cured by one or more of light, UV, heat, or the like.

Coating a thin, flexible substrate with biocompatible material is not trivial because the substrate may need to be coated on the side where electronic components are positioned and on the opposite side. In addition, the substrate may need to be coated evenly and comprehensively (for example, the substrate may be encapsulated by the biocompatible coating).

Coating can be applied by a device which can spray the coating material on both sides of the substrate or sheet 430. The coating can be evenly applied to encapsulate one or both sides of the substrate or sheet and its sides.

In some embodiments, acrylated urethanes can be used as coating material as these polymers have suitable adhesive properties and extensibility.

In some embodiments, it may be desirable for a substrate and electronic components supported by the substrate to be conformable as the substrate and the electronic components are intended to be positioned on or in the body. One property of conformability is the extensibility of the coating material as the electronic components may need to be isolated from the wound. Coating applied to the substrate may need to have the ability to stretch with the substrate. Pairing the elongation characteristics of both the substrate and coating can maximize the desired properties of the device. In some examples, the substrate can be formed from TPU film Coating can be formed from one or more suitable polymers, adhesives, such as 1072-M adhesive (for example Dymax 1072-M), 1165-M adhesive (such as, NovaChem Optimax 8002-LV, Dymax 1165-M, or the like), 10901-M adhesive (for instance, Dymax 1901-M or 9001-E Dymax), parylene (such as, Parylene C), silicones, epoxies, urethanes, acrylated urethanes, acrylated urethane alternatives (such as, Henkel Loctite 3381), or other suitable material.

In some embodiments, the substrate (for example, TPU) may by hydrophilic and, accordingly, may need to be encapsulated in hydrophobic coating to create a hydrophobic dressing to be placed on or in the wound.

In some embodiments, the coating can be substantially stretchable or extensible. In some embodiments, certain regions or different sides of the sheet 430 can have the same or different coatings. In some embodiments, non-stretchable or substantially non-stretchable coating can be applied to at least some of the plurality of electronic components of the sheet 430. In some embodiments, non-stretchable or substantially non-stretchable coating can be applied onto a connecting track 410. Alternatively or additionally to coating the track 410, an electronic module 402 can also be coated by a non-stretchable or substantially non-stretchable coating. Non-stretchable or substantially non-stretchable coating described herein can be formed from acrylated or modified urethane material (such as, Henkel Loctite 3211). For example, coating can be one or more of Dymax 1901-M, Dymax 900 1-E, Dymax 20351, Dymax 20558, Henkel Loctite 3211, or another suitable material. Coating can have viscosity from about 13,500 cP to 50,000 cP before being cured or from about 3,600 cP to about 6,600 cP before being cured. In some cases, coating can have viscosity of no more than about 50,000 cP. Coating can have hardness from about D40 to about D65 and/or linear shrinkage of about 1.5-2.5%. Coating can be transparent or substantially transparent to permit optical detection. Coating may be colorless or substantially colorless. Coating can be fluorescent. Coating can retain bond strength when subjected to sterilization, such as EtO sterilization.

In some embodiments, a single layer or multiple layers of adhesives can be applied. In some embodiments, a single layer of stretchable or non-stretchable coating can be applied. In some embodiments, multiple layers of stretchable or non-stretchable coating can be applied. For example, multiple layers of coating can be applied to achieve desired stiffness or rigidity.

Embodiments of the coatings and components for sensor enabled sheets or substrates for use in wound dressings, wound dressing components, wound treatment apparatuses and methods described herein may also be used in combination or in addition to those described in International Application No. PCT/EP2018/059333, filed Apr. 11, 2018, titled COMPONENT STRESS RELIEF FOR SENSOR ENABLED NEGATIVE PRESSURE WOUND THERAPY DRESSINGS, and International Application No. PCT/EP2018/069883, filed Jul. 23, 2018, titled BIOCOMPATIBLE ENCAPSULATION AND COMPONENT STRESS RELIEF FOR SENSOR ENABLED NEGATIVE PRESSURE WOUND THERAPY DRESSINGS," the disclosures of which are hereby incorporated by reference in their entireties.

As described herein, the placement of components and adhesives applied to the sheet 430 can be applied in certain predetermined configurations. Additionally, the coating of the sheet 430 and components of the sheet 430 can be required to fully encapsulate or partially encapsulate the components and/or sheet. The coating can also be required to be applied uniformly or in varied patterns depending on the type of coating or adhesive and the desired material characteristics. Therefore, it can be desirable to inspect and confirm application and coverage of the adhesive or coatings of the sheet 430 and components of the sheet 430 as well as inspect and confirm the proper placement of the components of the sheet 430.

Inspection of Encapsulated Electronic Components

Coated electronic components, including flexible circuit boards, including but not limited to those described herein with respect to wound dressings and wound therapy systems, are inspected for proper manufacturing and coating of the components. In some embodiments, the circuit board can be extensible. In some embodiments, the flexible and/or extensible circuit boards can be used similar to the use of flexible circuit boards as described herein. The coating materials and/or adhesives can be transparent and it can be difficult to identify defects or insufficient coverage of the coating or adhesives. Additionally, it could be helpful to inspect and confirm placement of components on a flexible circuit board.

Embodiments of the present application include methods of manufacturing and methods and systems for inspection that facilitate confirming the presence and/or location of coatings and/or electronic components. While the embodiments are described with respect to electronic components on medical devices such as wound dressings, it will be appreciated that these methods and systems may be applicable to non-medical devices as well.

In some embodiments, the electronic components and/or flexible circuit boards can utilize an adhesive and/or coating that fluoresces when exposed to ultraviolet (UV) light. In some embodiments, the coating or adhesive can have a fluorophore added to the coating or adhesive material. In some embodiments, the coating or adhesive can fluoresce when excited by UV and/or visible light. The fluorescing material can enable inspection of the electronic components by confirming full coverage of the coating or adhesives or detecting defects in the coatings or adhesives. Further, in some embodiments, the use of a fluorescing material coating or adhesives can also allow inspection to confirm placement of the components on a flexible circuit board. For example, the use of an optically transparent fluorescing material can allow the confirmation of placement of components and integrity of tracks after coating. The fluorescing material can enable inspection of the sufficiency or defects in the coating or adhesives applied to the flexible and/or extensible circuit boards. Additionally or alternatively, visual inspection through the visibly transparent coating of the underlying electronic connections or tracks and electronic components after coating can be used to ensure no displacement.

As is used herein, printing material on a printed circuit board, sheet, or substrate can include one or more of laminating, adhering, or any other suitable technique. In some embodiments, the adhesives or coatings can be applied to any flexible printed circuit board and/or components on the flexible printed circuit board. In some embodiments, the flexible circuit board can be similar to the sensor array sheet 430 described herein that is flexible as well as extensible.

In some embodiments, the coating and/or adhesive applied to the PCB can be formed from a material that will fluoresce when exposed to UV light, sometimes referred to herein as a UV-initiated fluorescing material. In U.S. Provisional Application 62/556,479 to which this application claims priority, a material with UV initiators in them or a UV initiating material was defined as any material that would react and/or fluoresce when exposed to UV light, which includes UV-initiated fluorescing materials as well as materials that would react when exposed to UV light but not necessarily fluoresce, such as materials that will cure when exposed to UV light. In some embodiments, UV-initiated fluorescing material may cure under UV light or can be cured by one or more of light, UV, heat, or the like as described herein. In some embodiments, the coating and/or adhesive applied to the PCB can be formed from acrylated urethane or other material, such as 1072-M adhesive (for example Dymax 1072-M), 1165-M adhesive (such as, NovaChem Optimax 8002-LV, Dymax 1165-M, or the like), 10901-M adhesive (for instance, Dymax 1901-M or 9001-E Dymax), parylene (such as, Parylene C), silicones, epoxies, urethanes, acrylated urethanes, acrylated urethane alternatives (such as, Henkel Loctite 3381), other suitable biocompatible and substantially stretchable materials, or another suitable material as described herein. In some embodiments, the coating and/or adhesive applied to the PCB can be an adhesive, biocompatible coating, or a non-stretchable or substantially non-stretchable coating to provide stress relief for the electronic components, or any other coating described herein. Additional embodiments of the coatings that can be used with the apparatuses and methods described herein can be found in International Application No. PCT/EP2018/059333 and International Application No. PCT/EP2018/069883, the disclosures of which are herein incorporated by reference in their entireties.

Figure 5A:
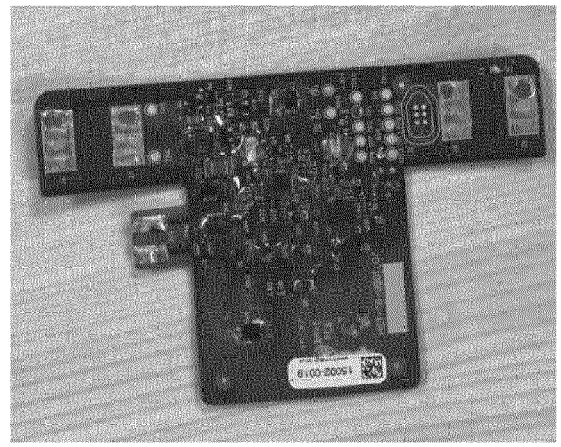
FIGS. 5A-5B illustrates an embodiment of a flexible printed circuit board with UV initiated material coating or adhesive.
Figure 5B:

FIGS. 5A-5B illustrate an embodiment of a printed circuit board (PCB) 500 with electronic components coated in one or more suitable polymers, adhesives, such as 1072-M adhesive (for example Dymax 1072-M), 1165-M adhesive (such as, NovaChem Optimax 8002-LV, Dymax 1165-M, or the like), 10901-M adhesive (for instance, Dymax 1901-M or 9001-E Dymax), parylene (such as, Parylene C), silicones, epoxies, urethanes, acrylated urethanes, acrylated urethane alternatives (such as, Henkel Loctite 3381), or other suitable biocompatible and substantially stretchable materials. As illustrated in FIG. 5A, the coating can be transparent which can make it hard to detect where the coating has been placed for inspection. In some embodiments, the flexible PCB can be coated with a UV initiated material. In some embodiments, the UV initiated material can include an acrylated polyurethane, other material described herein, or other materials that will fluoresce when exposed to UV light. The coated electronics and printed circuit board can be subjected to UV exposure and the florescence of the coating or adhesive material can identify where the coating or adhesive has been placed on the sample. FIG. 5B illustrates the coated electronics of FIG. 5A fluorescing under UV light as visible blue light to identify the regions covered with coating or adhesive. In FIG. 5B, the underlying electronics covered by the coating are visible under UV light because of the blue fluorescence. In some embodiments, the underlying components are visible when the polymer is fluorescing. In some embodiments, the electronics covered by the coating can be partially obscured but the outline of the components can be visible as illustrated in FIG. 5B.

Figure 6A:
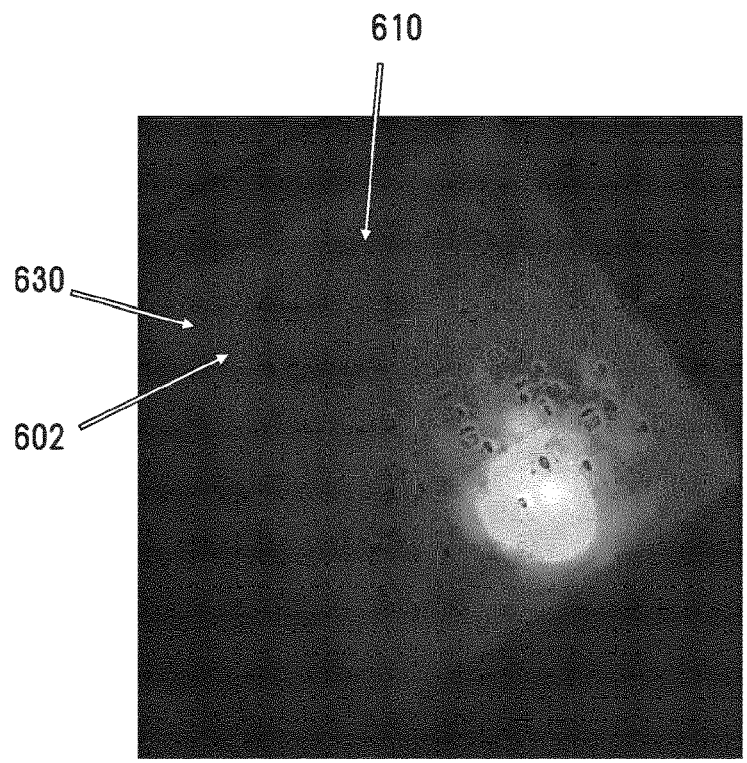
FIGS. 6A-6D illustrates a flexible sensor array printed circuit with UV initiated material coating or adhesive under UV light.
Figure 6B:
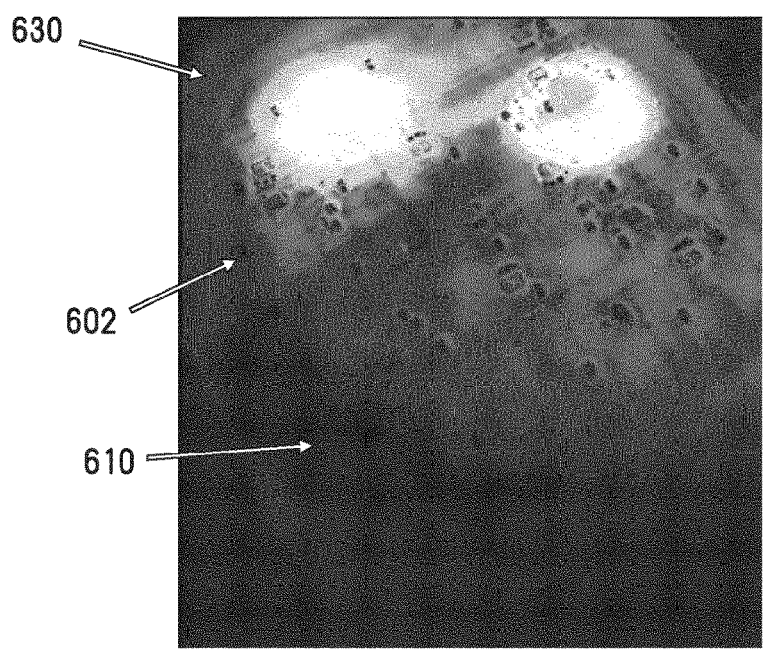

FIGS. 6A-6D illustrate a flexible sensor array printed circuit with a UV-initiated fluorescing material coating or adhesive that is optically transparent and will fluoresce under UV light which can enable detection of full coverage and proper placement on the sensors. FIGS. 6A-6D illustrate a flexible sensor array printed circuit or sheet similar to the flexible sensor array printed circuit or flexible sensor sheet described with reference to FIGS. 4A-4B. The flexible sensor sheet can be coated with a UV-initiated fluorescing material, which allows the coating or adhesive material to be visible under UV light. The UV-initiated fluorescing material can fluoresce a color in the visible spectrum (e.g., as visible blue light). The bright spots shown in FIGS. 6A-6B are created by localized light beams onto the coating.

In some embodiments, the UV-initiated fluorescing material can include an acrylated polyurethane or other material that will fluoresce when exposed to UV light. FIG. 6A-6D illustrate the flexible PCB or sheet 630 configured to support one or more electronic components, including an electronic component or module 602 with a plurality of connectors and a plurality of electronic connections 610. As illustrated in FIGS. 6A-6D, the portions or regions of the flexible PCB or sheet 630 incorporating the electronic components 602 and electronic connections 610 are shown as darker regions and are visible due to the fluorescence of the coating or adhesive material, which emits a visible light (as illustrated, a visible blue light). This visible light may illuminate the electronic components and electronic connections through the coating or adhesive material. In some embodiments, the electronic components and electronic connections may be made of a reflective material, and the visible light emitted by the fluorescence of the coating may reflect off the reflective material. In some embodiments, the electronic components and electronic connections do not need to be made of a reflective material to be visible as the visible light emitted by the fluorescence of the coating can allow the electronic components and electronic connections to be visible. In some embodiments, this can allow for inspection of the arrangement and placement of the electronic components and connections on the flexible PCB while also allowing for inspection of the coating or adhesive material.

In some embodiments, the coating, the electronic components 602, and the electronic connections 610 of the flexible PCB or sheet can be visible by using UV light, visible light, and/or light of other wavelengths. In some embodiments, the coating's transparency or translucency can allow for inspection of components 602 and connections 610 using light wavelengths absent of the UV excitation wavelength, including at optical wavelengths. In some embodiments, the electronic components or connections can be visible under UV light through the coating material. The components 602 and connections 610 can be visible under visible light. In some embodiments, the coating, the electronic components 602, and electronic connections 610 of the flexible PCB or sheet can be visible using a combination of both UV excitation and visible wavelengths allowing the electronic components 602, connections 610 and coating integrity to be inspected at the same time. In some embodiments, the flexible PCB or sheet can be inspected only under UV excitation, only under visible light, or under a combination of both to enable visualization of one or more of the electronic components 602, connections 610 and coating integrity.

In some embodiments, even if only UV light is used, the light emitted or fluoresced can be visible blue light. This can allow the visualization of the coating as it fluoresces as well as the visualization of the electronic components and connections by illumination due to the emitted visible light. For example, even if no visible light is used, if the fluorescence is in the visible blue wavelength, it can allow for the electronic components 602 or connections 610 to be seen as if it were lit by blue light only. In some embodiments, it can be possible to choose the fluorescence wavelength emitted by the coating by adding different fluorescent molecules. For example, the coating can be made to fluoresce green or red.

In some embodiments, the inspection of the electronic components 602 and electronic connections 610 may be possible by transmission of light through the entire assembly with the light sensors being on the opposite side of flexible PCB or sheet to the light source. In some embodiments, the UV light can be transmitted from a light source on the same side of the flexible PCB or sheet as the light sensor.

In some embodiments, the flexible sensor array printed circuit board can have the components positioned in predetermined locations. In some embodiments, the fluorescence or color of a particular region of the coated PCB or sheet when exposed to UV light can allow for inspection of the proper configuration or placement of the components on the PCB or sheet. In some embodiments, different components or regions can have different coatings applied. For example, as described herein with reference to FIGS. 4A-4B, a pattern of adhesive regions can be used to equalize the stress or strain on the sheet. In some embodiments, the different coatings on the different components or regions can appear with a different fluorescence intensity or a different color when exposed to UV light, different wavelengths of UV light, or different wavelengths of UV and/or visible light. In some embodiments, the adhesive or coating described herein, including the first and second coatings described with reference to FIGS. 9A-9C can be a material that will fluoresce under UV and/or visible light. For example, if the inspection is intended to be visual or conducted by the eye, the excitation would be such that the Stokes Shift produces an emission in the visible wavelength range (typically 390-700 nm). Alternatively or additionally, the inspection could be done using instrumentation. This can allow a wider range of wavelengths to be used. The wavelength that is used to excite the material to fluoresce could be different wavelengths of UV, visible light, and/or any other wavelength that can excite the coating or adhesive material to fluoresce. In some embodiments, a grid or baseline color of the expected locations can be correlated with the color or florescence response of the PCB or sheet when exposed to UV or other light. There can be an expected color and/or intensity for shaped tracks or electronic components on the PCB or sheet. There can be a glow or color response expected for each component or region of the PCB or sheet which can allow for detection of defects in component arrangement as well as the coating and adhesive application. For example, if a coating, component, or track was at an incorrect location, the user would visualize a different color or florescence intensity than expected in that location which could indicate a defect in coating or component configuration.

In some embodiments, the inspection of the flexible PCB or sheet can be done with image based inspection of the PCB or sheet. In some embodiments, an image can be captured, saved, and displayed or viewed to inspect the coating and/or electronic components and connections. In some embodiments, an image of the flexible printed circuit board or sheet under UV and/or visible light can be captured by a camera or optical sensor. The image can be displayed on a display, for example, a computer screen, mobile device screen, or other device for displaying an image. In some embodiments, the image of the flexible printed circuit board under UV and/or visible light can be displayed on a display. In some embodiments, the image on the display can indicate the location of the coating material. In some embodiments, the image on the display can indicate the location of the electronic components or connections underneath the coating material. In some embodiments, a UV filter can be used while the flexible PCB or sheet is under a UV lamp. The UV filter can be tinted and stops UV damage to the eyes. In some embodiments, a single image can be used to view both the coating and electronic components and connections. In other embodiments, different images can be taken using different types of light.

The flexible PCB or sheet can be imaged only under UV excitation, only under visible light, or under a combination of both to enable visualization of one or more of the electronic components 602, connections 610 and coating integrity. In some embodiments, the coating, the electronic components 602, and electronic connections 610 of the flexible PCB or sheet 630 can be visible using a combination of both UV excitation and visible wavelengths allowing the electronic components 602, connections 610 and coating integrity to be inspected in a single image. In other embodiments, an image can be taken of the flexible PCB under each type of light. In some embodiments, the use of UV or visible light can be adjusted depending on which characteristics of the flexible PCB or sheet are being inspected.

Additionally, in some embodiments, a specific wavelength of light can be imaged for inspection processes. For example, a single blue wavelength can be imaged for inspection using the fluorescence of the coating or a single red wavelength can be imaged for inspection of the components or connections. In some embodiments, the visible component of the light can either be used at the same time or before/after the UV component of the light in order to image the electronic components and electronic connections. In some embodiments, different coating materials applied to the sheet can fluoresce different colors when exposed to UV light.

In some embodiments, the grid or baseline color of the expected coating, component, and connection locations can be correlated with the color or florescence response of the PCB or sheet when exposed to UV or other light. There can be a glow or color response expected for each component or region of the PCB or sheet which can be correlated with or compared to the actual image captured or displayed on the display to allow for detection of defects in component arrangement as well as the coating and adhesive application.

Figure 6C:
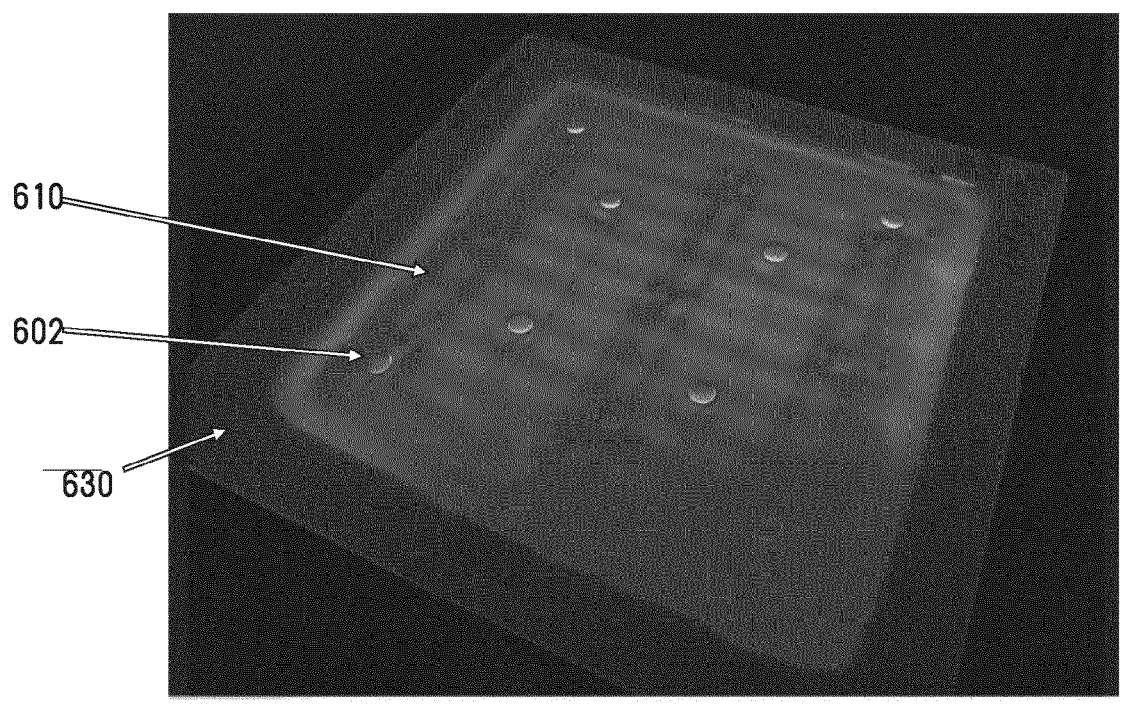
Figure 6D:
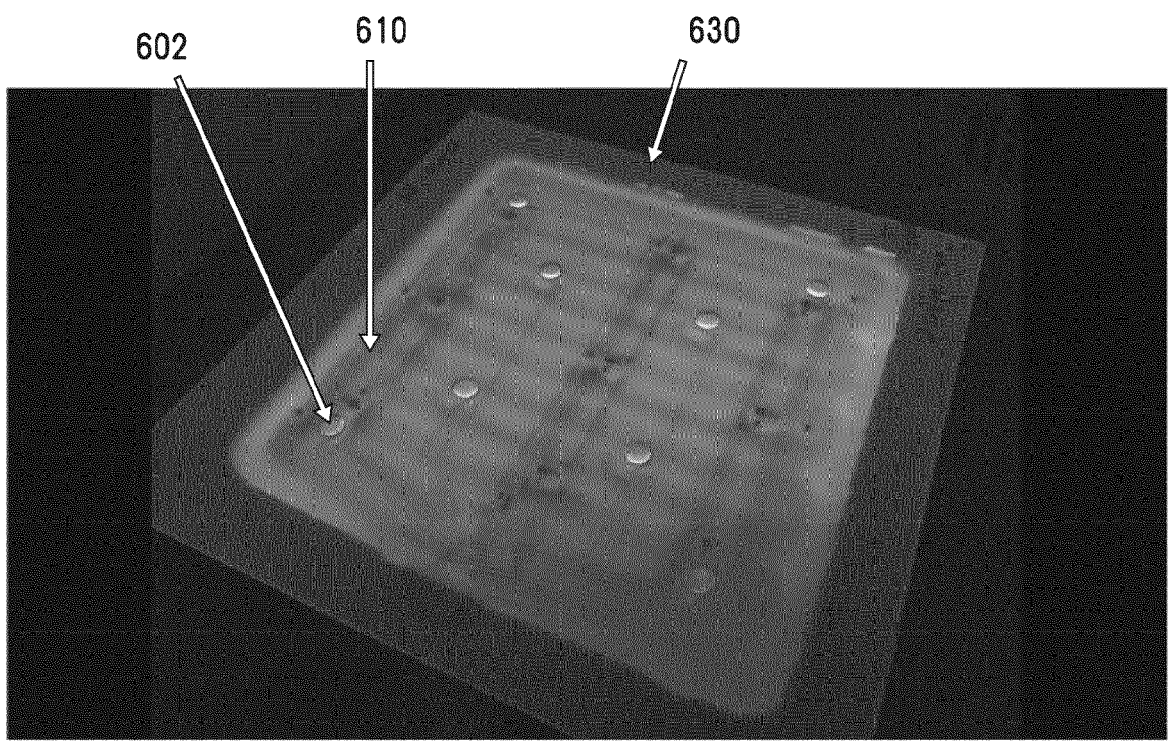

In certain circumstances, it can be important to ensure the proper coating and amount of coating and adhesive used for the PCB or sheet and the components of the PCB or sheet. If the adhesive or coating applied is too thick, it can increase the noise or otherwise hinder the data collection. However, if the adhesive or coating applied is too thin, it can fail to protect or insulate the electronic components. In some embodiments, the intensity of the fluorescence or color can allow for detection of not only the presence of coating or adhesive but also a visualization of the amount of adhesive or coating. In some embodiments, the intensity of the fluorescence or color can indicate that the type of coating applied is correct. Different types and different amounts of adhesives or coatings on the PCB or sheet can have different fluorescence intensities or colors. For example, too much fluorescence response can signify that too much coating or adhesive was applied to the PCB or sheet. In some embodiments, the intensity of the fluorescence or color can indicate there is not enough coating. FIGS. 6C-6D shows the fluorescence of the coating with the electronic components 602 and electronic connections 610 running up and down the sheet 630. The unevenness in the coating is shown by darker lines or gaps in fluorescence running left to right on the sheet 630 in FIGS. 6C-6D.

Figure 7A:
FIGS. 7A and 7B illustrate a flexible sheet with UV initiated material coating or adhesive under UV light.
Figure 7B:
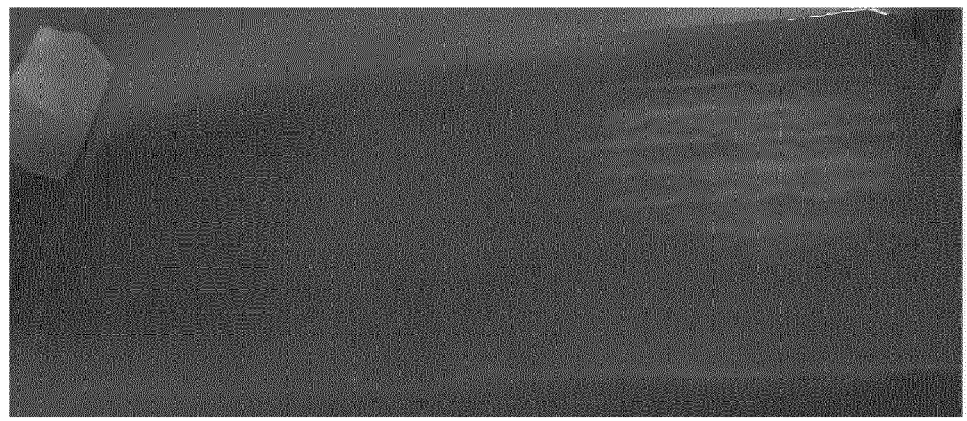

FIGS. 7A and 7B illustrate a flexible sheet similar to the flexible sensor array printed circuit described with reference to FIGS. 4A-4B. The flexible sensor sheet can be coated with a material that will fluoresce under UV light. The fluorescence of the UV initiated material coating or adhesive can show where the coating or adhesive has been applied. FIGS. 7A and 7B illustrates a flexible sheet with UV initiated material coating or adhesive under UV light which can enable detection of full coverage of the coating or adhesive. As illustrated in FIG. 7A, the fluorescence of the UV initiated material coating or adhesive shows that there is not full coverage of the sheet as shown by the gaps in fluorescence of the material layer. FIG. 7B illustrates a flexible sheet with full coverage of the UV initiated material coating or adhesive as shown by the full fluorescence of the material layer.

Figure 8A:
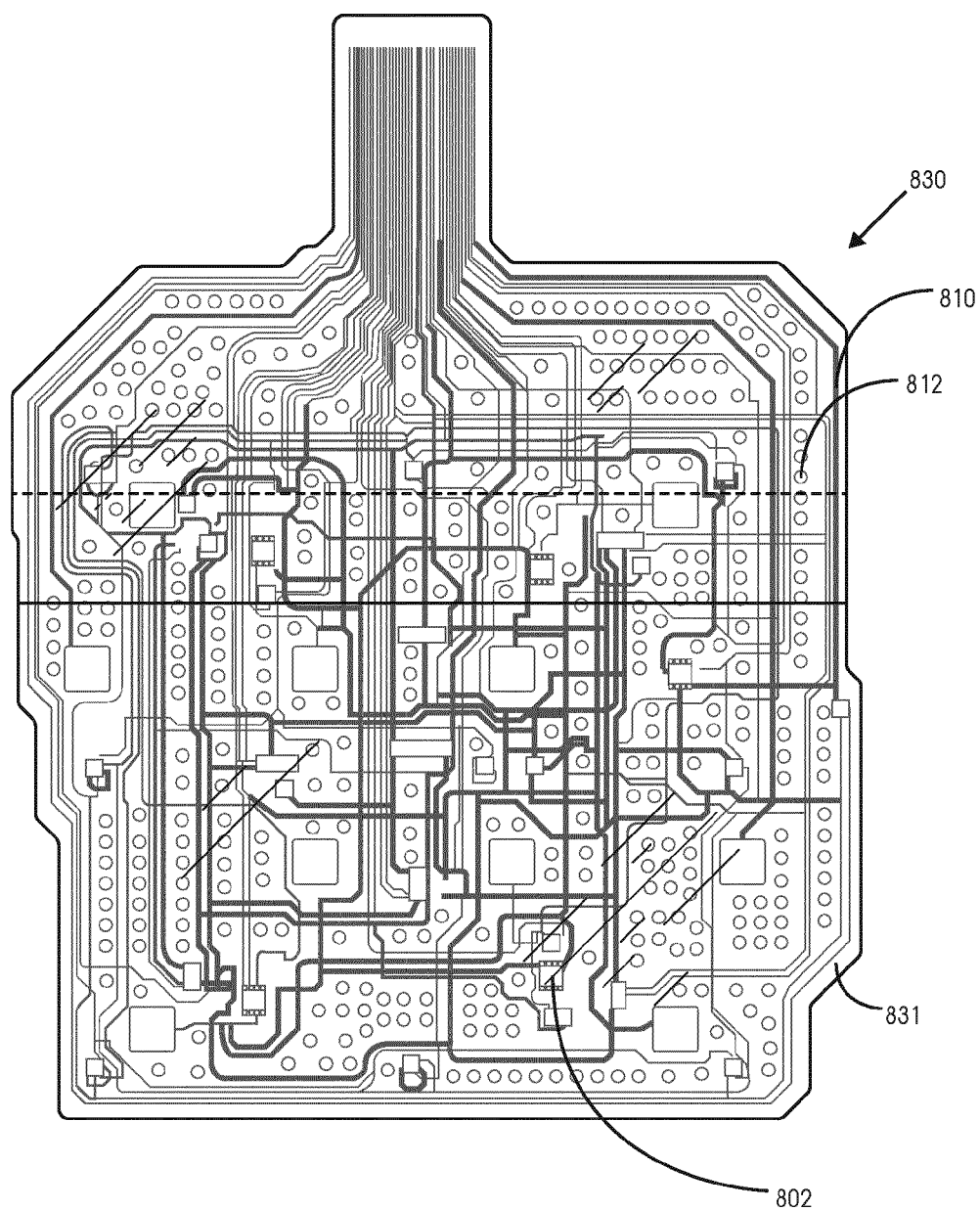
FIGS. 8A-8D illustrate an embodiment of a flexible sheet with the electronic components and electronic connections on the sheet.

In some embodiments, the sheet can be coated with a coating that is substantially stretchable or extensible. In some embodiment, the sheet can be coated or encapsulated in the substantially stretchable or extensible coating or adhesive. Defect identification in the substantially stretchable or extensible coating or adhesive encapsulation layer can be achieved by using a substantially stretchable or extensible coating or adhesive material that is made from or includes a material that can fluoresce when exposed to UV light. FIGS. 8A-8D illustrate a flexible sheet 830 with the electronic components 802 and electronic connections 810 on the sheet 830. The sheet 830 can have perforations 812 in areas of the sheet 830 not covered by the electronic components 802 and electronic connections 810. FIG. 8A illustrates an embodiment of a sheet 830 with electronic connections 810 running along the sheet connecting components 802 of the sheet 830. The perforations 812 can allow for fluid transmission through the sheet 830. The perforations can be positioned on an area of the sheet 830 that is not covered by the electronic connections 810 and the electronic components 802.

FIG. 8A illustrates the sheet 830 with a backing layer 831 that covers the wound facing side of the sheet 830. The backing layer 831 can be used to protect the sheet 830 and/or assist in application of the sheet 830 to a skin surface or a wound. The backing layer can be a temporary release liner on either or both sides of the sheet to provide mechanical rigidity and prevent extension and drape during processing, for example, whilst coating or encapsulating the side of the sheet with the electronic components and tracks on the sheet. The backing layer could assist with handling up to the point of application to the wound. As such it may have tabs, courtesy handles, folds, it may be slitted, overlapped, and may have numbers, markings, location identification, labelling, prohibitions and warnings or other instructions to aid with application compliance and disposal. In the case that the backing layer is used for processing and encapsulation of the electronic side, the backing layer may be discarded and a new (or the same) release handle placed over the side of the sheet with the coated electronics. In other embodiments, the backing layer could be left on resulting in a coated sheet sandwiched between release handles.

Figure 8B:
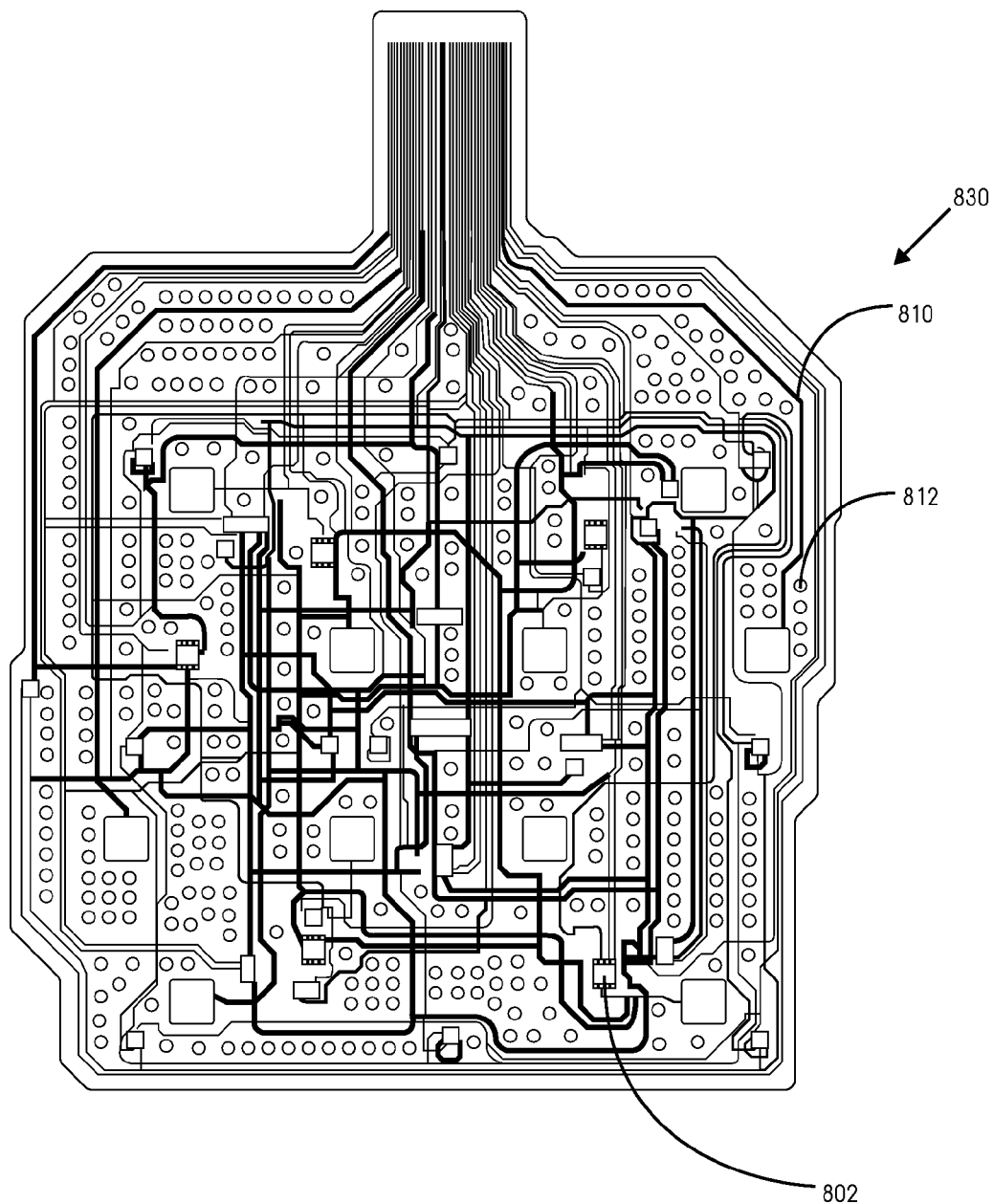
Figure 8C:
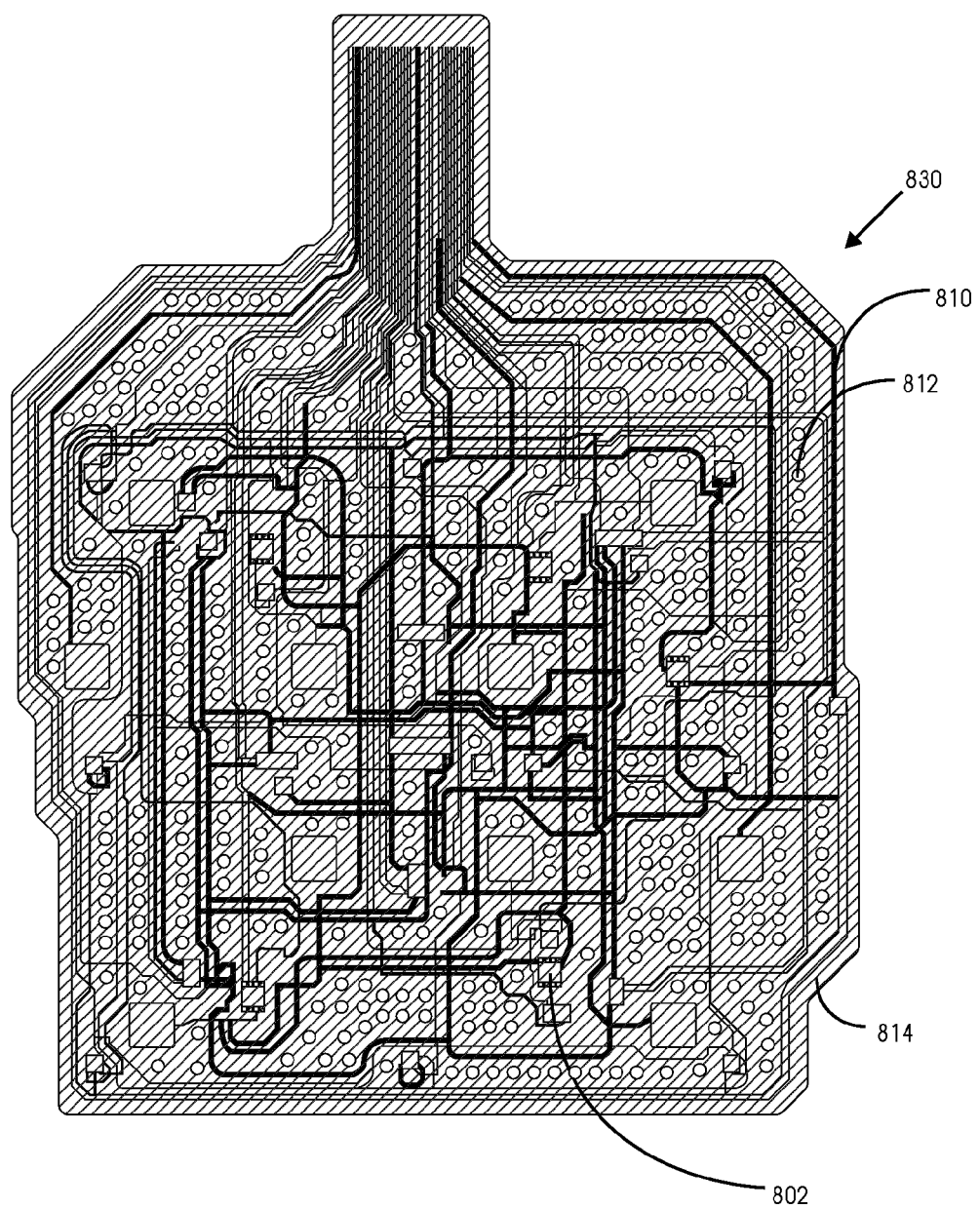
Figure 8D:
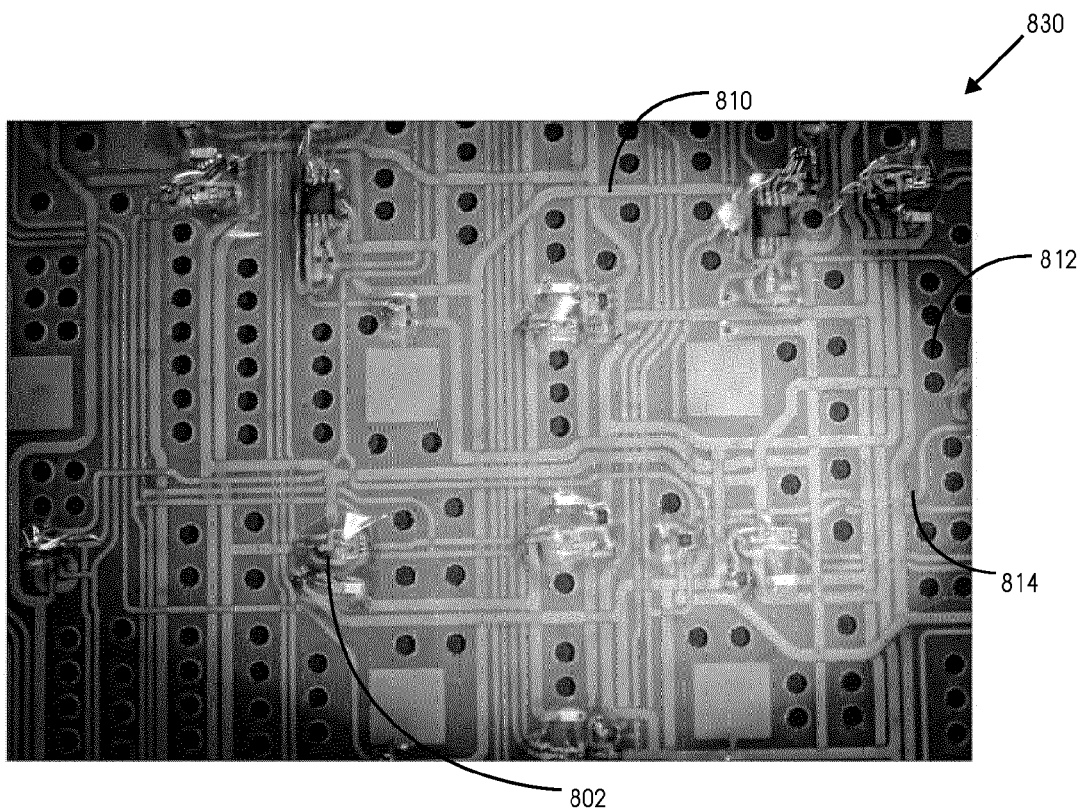

FIG. 8B illustrates a sheet 830 with the backing layer removed. FIGS. 8C and 8D illustrate the sheet 830 coated with an adhesive or coating 814 that fluoresces under UV light. In some embodiments, the coating that fluoresces under UV light can be the substantially stretchable or extensible coating or adhesive that encapsulates the sheet 830 as shown in FIGS. 8C and 8D. As illustrated in FIGS. 8A-8D, the substantially stretchable or extensible coating or adhesive does not cover the perforations 812 of the sheet 830. In some embodiments, the coating or adhesive will be applied to a non-perforated sheet. The sheet can then be perforated through the coated sheet. The perforations can be formed through one or more suitable methods, such as a laser perforation process, cold pin perforation, hot pin perforation, dye cut, and/or stamp out.

Figure 9A:
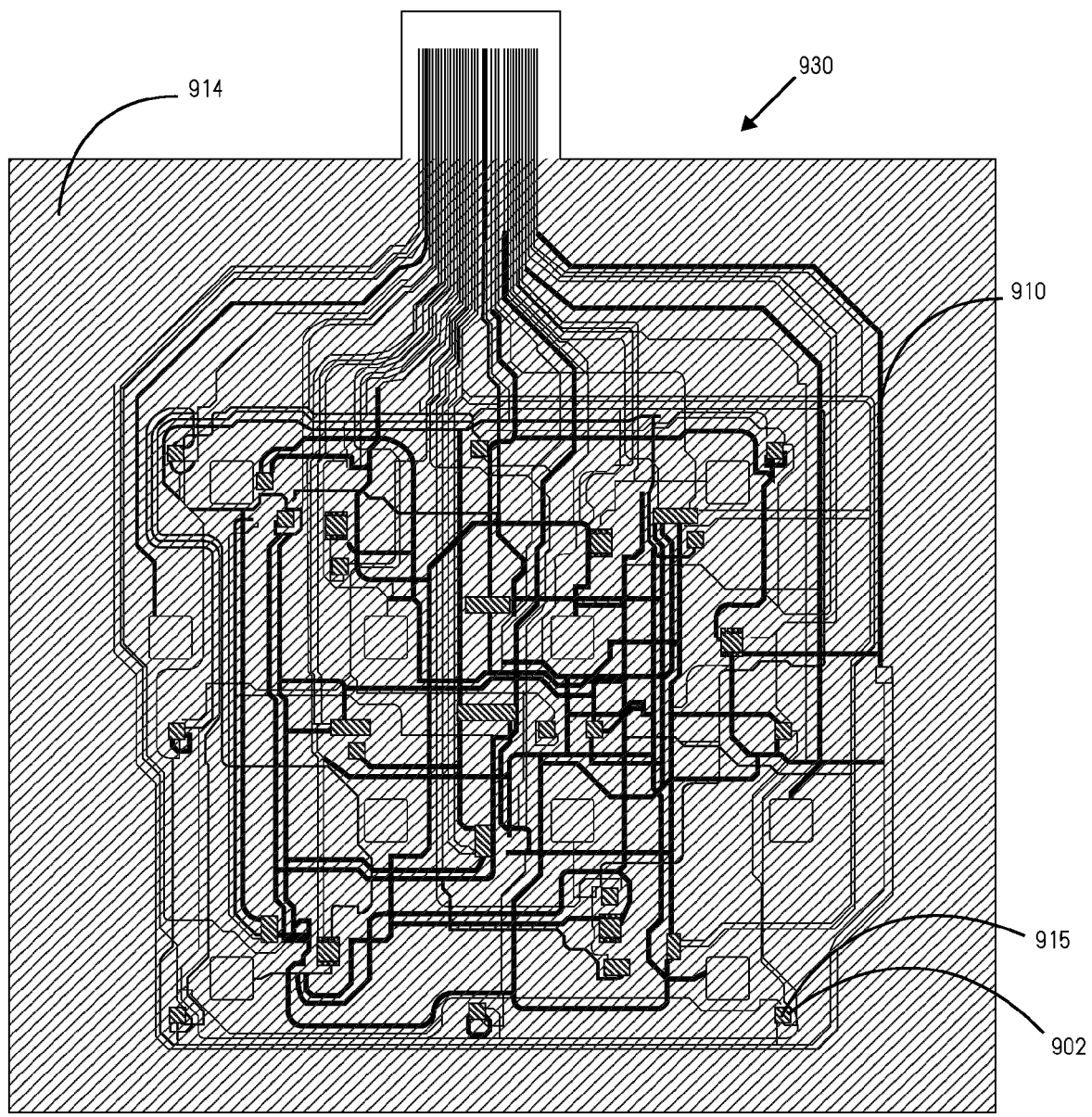
FIGS. 9A-9C illustrate embodiments of a sheet coated with an adhesive or coating that fluoresces under UV light.
Figure 9B:
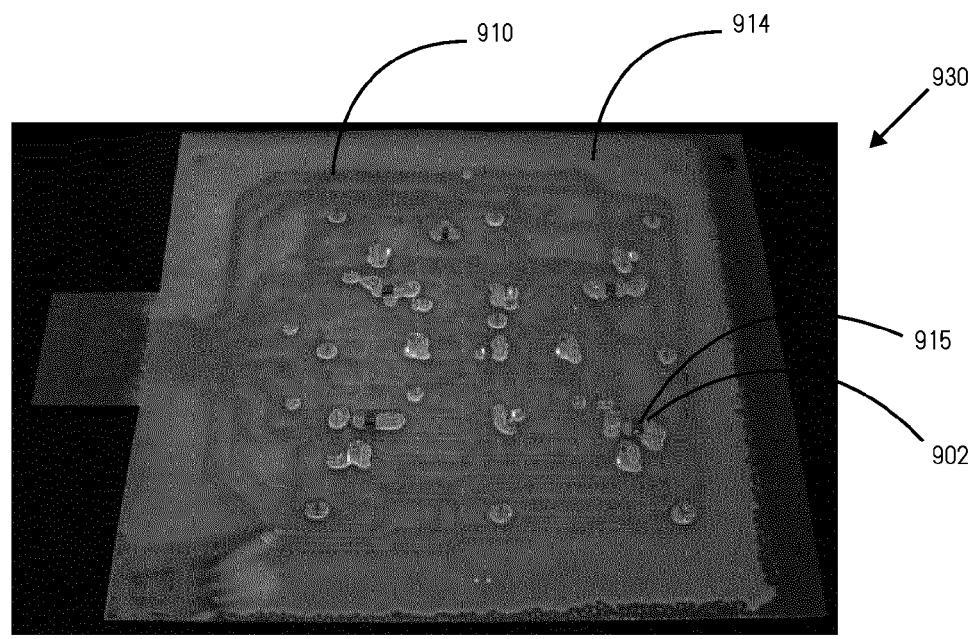
Figure 9C:
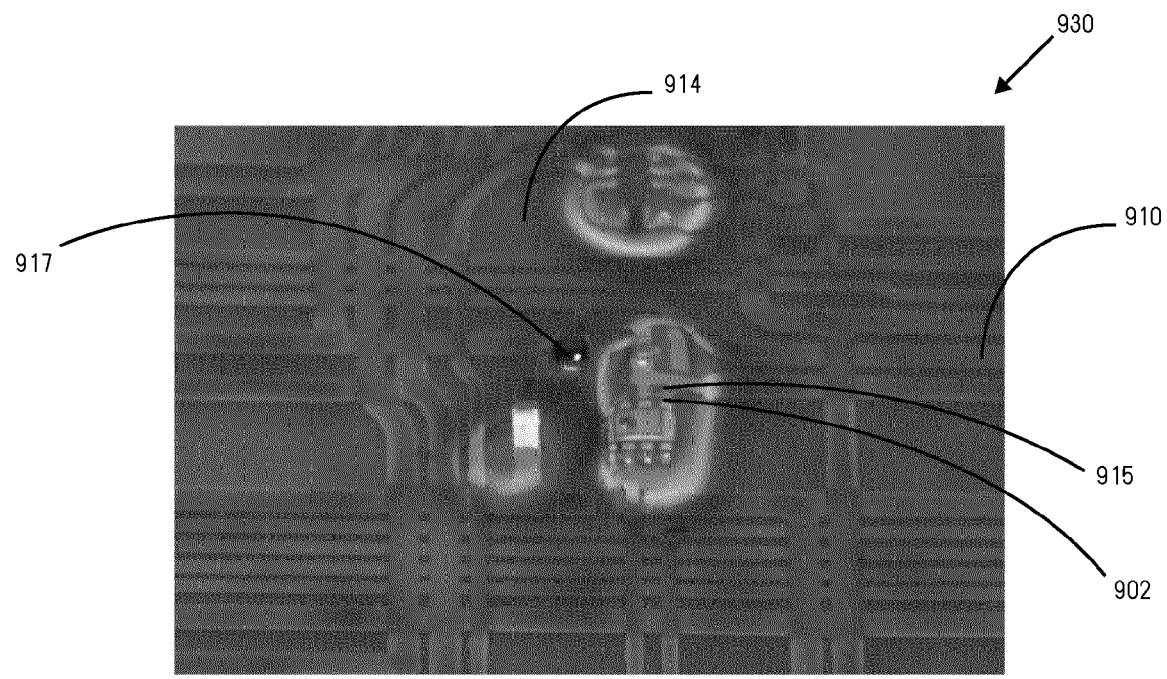

As described previously, in some embodiments, certain regions or different sides of the sheet can have the same or different coatings. In some embodiments, in addition to or alternatively, a non-stretchable or substantially non-stretchable coating can be applied to at least some of the plurality of electronic components of the sheet. FIG. 9A-9C illustrate a sheet 930 with a connecting track 910, and electronic module 902. FIG. 9C is a close-up view of a portion of the sheet 930 shown in FIG. 9B. The sheet 930 can include a first coating 914 that is a substantially stretchable or extensible coating or adhesive and a second coating 915 that is a non-stretchable or substantially non-stretchable coating or adhesive. As illustrated in FIGS. 9A-9C, the non-stretchable or substantially non-stretchable coating 914 can be applied onto an electronic module 902. Alternatively or additionally to coating the electronic module 902, a connecting track 910 can also be coated by a non-stretchable or substantially non-stretchable coating. In some embodiments, the first coating 914 can be applied before or after the second coating 915. For example, the second coating 915 can be applied to the sheet first and the first coating 914 can be applied second and can cover the second coating 915. In other embodiments, the first coating 914 can be applied to the sheet first and the second coating 915 can be applied after.

In some embodiments, the first and/or second coating 914, 915 can be a material that will fluoresce under UV light or can be a material that contains a moiety that will fluoresce. In some embodiments, the first coating 914 can fluoresce a different color than the second coating 915. The pair of colors can be selected so as to be readily distinguishable by eye and the polymers can be selected so that the first coating 914 does not substantially absorb the light emitted by the second coating 915. For example, if the second coating 915 emitted in the blue, and the first coating 914 absorbed in the blue and emitted in the red, this could cause a problem. The coatings can be optically transparent so as to allow visual inspection of the components. As illustrated in FIGS. 9A-9C the first coating 914 can be a substantially stretchable or extensible coating or adhesive and when exposed to UV light can fluoresce a first color (e.g., blue) and the second coating 915 can be a non-stretchable or substantially non-stretchable coating and when exposed to UV light can fluoresce a second color (e.g., red). In FIG. 9A, the two colors are noted by the different hash marking of certain regions. In other embodiments, the first coating 914 can fluoresce the same color as the second coating 915. In some embodiments, the first coating 914 can fluoresce the same color as the second coating 915 but at different intensities to distinguish between the two coatings of the same color.

FIGS. 9B and 9C show images of the sheet 930 with the first coating 914 and the second coating 915 under UV light. The first coating 914 is shown as the material that overlays substantially the entire surface of the sheet 930. The second coating 915 is shown as the material that is fluorescing a different color and in FIG. 9C is presented as a brighter color in small regions or dots throughout the sheet 930. FIG. 9C illustrates the sheet 930 with the two coatings. The sheet 930 can include a first coating 914 that is substantially stretchable or extensible coating or adhesive and a second coating 915 that is a non-stretchable or substantially non-stretchable coating or adhesive. The fluorescence of the coating can be used to visualize imperfections or areas of the sheet 930 with imperfect coating. For example, FIG. 9C illustrates an electronic module 917 that was not coated or sufficiently covered with the second coating 915 as illustrated by the lack of fluorescence from the second coating 915 in that area of the sheet 930.

FIGS. 9A-9C illustrate the inspection of the sheet 930 through UV fluorescence. As illustrated in FIGS. 9A-9C, the first coating 914 can fluoresce a first color (e.g., blue) when exposed to UV light and the second coating 915 can fluoresce a second color (e.g., red) when exposed to UV light. This can allow a clear distinction to be made between the two materials during visual inspection. This can also allow for errors in the coating to be easily visible as illustrated in FIG. 9C.

In some embodiments, the coating or adhesive material can include fluorophores at various emission wavelengths. In some embodiments, a fluorophore can be added to any of the coatings or adhesives described herein. Each coating or adhesive could have a fluorophore of a different wavelength. This can allow for a visual assessment of the different coatings. In some embodiments, only one of the coatings or adhesives could have a fluorophore. For example, the first coating 914 can have no emission or no fluorescence when exposed to UV light and the second coating 915 can include a fluorophore and emit a color when exposed to UV light. In some embodiments, the fluorophore may be dispersed in the polymer coating or adhesive in the form of beads, granules, or other locally contained media (e.g. fluorescent microparticles, microbeads or quantum dots). For the use of the sheet as a medical or wound care device the fluorophore can be biocompatible. Alternatively or additionally, the fluorophore could be encapsulated in a biocompatible coating. In some embodiments, the fluorophore in the coating or adhesive may be non-leachable/extractable from the coating or adhesive in physiological fluids or suitable test fluids, for example polar and a non-polar extract media, or, for example as described in ISO 10993. In some embodiments, the substance is not on the United Kingdom's Medicines and Healthcare products Regulatory Agency's (MHRA's) list of active substances.

The first coating 914 and the second coating 915 can have different emission wavelengths. For example, the first coating 914 that is substantially stretchable or extensible coating or adhesive can emit blue visible light and the second coating 915 that is a non-stretchable or substantially non-stretchable coating or adhesive can emit red visible lights. Other combinations could also be used, including no fluorescence from one of the coatings. In some embodiments, the fluorescence emission wavelength of the second coating could be the same as for the first coating. In some embodiments, the emission intensity of the second coating could be matched with that of the first coat.

Void space identification in the coatings or adhesives can be achieved using the fluorescent properties of the substantially stretchable or extensible coating or adhesive and/or the non-stretchable or substantially non-stretchable coating or adhesive. In some embodiments, providing a coating or adhesive material that can fluoresce under UV light can allow for visualization of voids in the coating by identifying a region of the sheet where there is no fluorescence emission. For gas bubble identification, in the substantially stretchable or extensible coating or adhesive (where the gas bubble is not over or under an opaque electronic module or track) optical transmission would be more effective at detecting a gas bubble in the substantially stretchable or extensible coating or adhesive coating. In some embodiments, gas bubble identification in the non-stretchable or substantially non-stretchable coating or adhesive can also utilize optical transmission to detect a gas bubble in the coating. For example, a gas bubble can be visualized and identified by observing or measuring the transmission of the light or color or intensity of the coating. When a gas bubble is present, the color or intensity of the coating would vary from the color or intensity of the coating in an area of the sheet without a gas bubble. In some embodiments, the same techniques described herein can be used for detecting a foreign object in the substantially stretchable or extensible coating or adhesive and/or the non-stretchable or substantially non-stretchable coating or adhesive. In some embodiments, foreign objects can also be identified by optical transmission, reflection, and/or direct imaging (i.e. photography).

If the void space or gas bubble is located under a component, the void space or gas bubble could cause failure of the component. To identify a void space or gas bubble under a component when the sheet is transparent, the sheet can be viewed optically from under the component on a side of the sheet opposite the components on the sheet. The void space or gas bubble can be seen optically through the transparent sheet.

As discussed previously, the coatings or adhesives can be applied by a robotic spray head which moves in the x/y axis in a serpentine pattern while spraying the coating or adhesive on the substrate. The linear serpentine pattern leads to a heterogenous topographic coverage in the form of peaks and troughs in the same orientation as the serpentine. This has become known as the "ploughed field effect." This can lead to inconsistent reading on the impedance pads but the effect can be minimized with the appropriate spraying settings or parameters on the controller controlling the robotic spray. Other patterns of coating can be used. For example, following the perimeter of the square sheet and indexing inwards or repeat parallel runs down one axis could be used. Since the sheet can be transparent, it can be difficult to visually assess the heterogeneity of the coating on the surface of the sheet once the sheet has been coated. It can be helpful to provide a method of inspection for both qualifying the process to ensure a spray pattern is devised which minimizes heterogeneity and also as a means of inspection during manufacture to ensure the desired output is maintained.

Figure 10A:
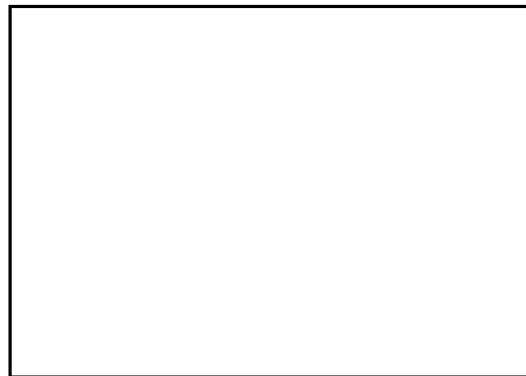
FIGS. 10A-10C illustrates an experimental setup of a sheet or other material coated with one or more coatings or adhesives.
Figure 10B:
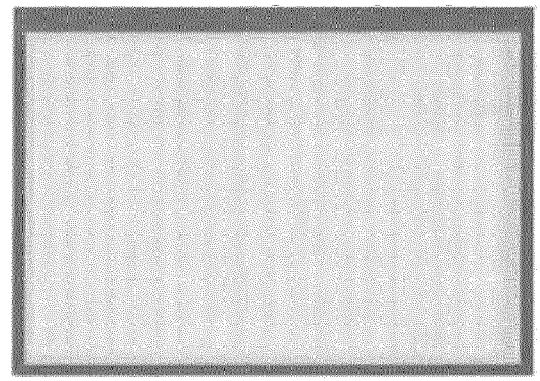
Figure 10C:
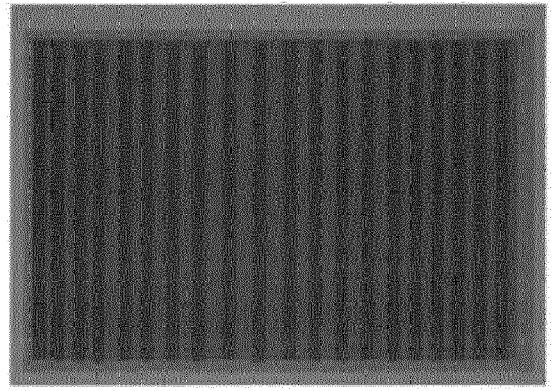

In some embodiments, the substantially stretchable or extensible coating or adhesive as described herein can be used to coat and/or encapsulate the sheet and can fluoresce when under UV light. As described herein, the substantially stretchable or extensible coating or adhesive's fluorescent properties under UV light can make the inspection process of the sheet easier. In some embodiments, to visually assess the coating on the sheet, the sheet can be placed over an orange substrate. In some embodiments, the orange substrate is a piece of orange paper. The coating or adhesive can be exposed to UV light and the coating or adhesive can fluoresce when exposed to UV light. This visual assessment technique utilizing the fluorescent property of the coating or adhesive or fluorescent materials embedded in the coating or adhesive can make the peaks and troughs created by the spraying or application process much easier to assess visually. FIGS. 10A-10C illustrate an experimental setup of a sheet or other material coated with one or more coatings or adhesives as described herein. The sheet in FIGS. 10A-10C is transparent. FIG. 10A illustrates an embodiment of the sheet or other material encapsulated in a coating or adhesive as described herein that is also transparent. FIG. 10A illustrates an embodiment of the transparent sheet encapsulated in the transparent coating or adhesive against a colorless backdrop, without fluorescence. FIG. 10B illustrates an embodiment of the sheet or other material encapsulated in a coating or adhesive against a color backdrop (e.g., orange backdrop), without fluorescence. FIG. 10C illustrates an embodiment of the sheet or other material encapsulated in a coating or adhesive against a color backdrop (e.g., orange backdrop), with fluorescence. The color backdrop can be used to quantify the heterogeneity. As illustrated in FIGS. 10A-10C, the color backdrop with fluorescence allows for greater contrast during visualization of the heterogeneity of the coating. The color backdrop can be applied by using a colored material behind the sheet. In other embodiments, a visualization system can be used with software which can assess the intensity of the color coming through the adhesive and quantify the heterogeneity.

Additionally or alternatively to the inspection by fluorescence, the coating can be inspected for sufficiency to electrically protect the components. In some embodiments, testing of the flexible printed circuit board can be conducted utilizing an electrostatic air discharge plate or probe. In some embodiments, a high voltage plate would be placed over the coated flexible PCB or coated sheet with the sheet connectors grounded. If the conformal coating is insufficient then the electrostatic discharge (or corona discharge) would short through the coating, both identifying the error and in some cases putting the PCB or sheet beyond use. In some embodiments, an image can be captured to detect where the corona discharge is located on the flexible PCB or sheet. If the coating of the flexible PCB or sheet is sufficient and correctly applied, then the test would be non-destructive.

In some embodiments, the coatings, adhesives, and components described herein with reference to the flexible and/or extensible sensor array printed circuit or flexible sheets of FIGS. 3A-3B, 4A-4B, and 6A-7B can be applied to any flexible circuit board or printed circuit board. For example, the coatings, adhesives, and components described herein with reference to the flexible sensor array printed circuit or flexible sheets of FIGS. 3A-3B, 4A-4B, and 6A-7B can be applied to printed circuit boards similar to the printed circuit boards of FIGS. 5A-5B. As described herein, the fluorescence inspection technique of the adhesives, coatings, and component placement utilizing UV initiated material of the adhesives or coatings of a flexible sensor array printed circuit or flexible sheets of FIGS. 3A-3B, 4A-4B, and 6A-7B can be used for inspection of coatings, adhesives, and components of any flexible circuit board or printed circuit board.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

All of the features disclosed in this specification (including any accompanying exhibits, claims, abstract and drawings), or all of the steps of any method or process so disclosed, may be combined in any combination, except combinations where at least some of such features or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future. The language of the claims is to be interpreted broadly based on the language employed in the claims and not limited to the examples described in the present specification or during the prosecution of the application, which examples are to be construed as non-exclusive. The scope of the present disclosure is not intended to be limited by the specific disclosures of preferred embodiments herein, and may be defined by claims as presented herein or as presented in the future.

What is claimed is:

1. A flexible sensor sheet for use on a wound, comprising:
   a flexible substrate;
   electronic components including one or more sensors positioned on the flexible substrate for detecting wound characteristics; and
   a first material coated on a first portion of the flexible substrate, wherein the first material is configured to fluoresce when exposed to UV or visible light and a second material coated on a second portion of the flexible substrate, wherein the second material is configured to fluoresce when exposed to UV or visible light, wherein the first material is different than the second material; and
   wherein the first material is a non-extensible material and the second material is an extensible material.

2. The flexible sensor sheet of claim 1, wherein the first material and the second material that will fluoresce when exposed to UV or visible light comprises an adhesive material.

3. The flexible sensor sheet of claim 1, wherein the first material and the second material that will fluoresce when exposed to UV or visible light comprises an acrylated polyurethane.

4. The flexible sensor sheet of claim 1, wherein the first material is configured to fluoresce a first color and the second material is configured to fluoresce a second color different from the first color.

\* \* \* \* \*